(12) United States Patent
Jellie

(10) Patent No.: US 6,962,579 B2
(45) Date of Patent: *Nov. 8, 2005

(54) SUBSTANCE DELIVERY DEVICE

(75) Inventor: Hugh Philip Jellie, Cambridge (NZ)

(73) Assignee: Advanced Animal Technology Limited, Hamilton (NZ)

(*) Notice: Subject to any disclaimer, the term of this patent is extended or adjusted under 35 U.S.C. 154(b) by 0 days.

This patent is subject to a terminal disclaimer.

(21) Appl. No.: 10/131,674

(22) Filed: Apr. 22, 2002

(65) Prior Publication Data

US 2002/0165488 A1 Nov. 7, 2002

Related U.S. Application Data

(60) Continuation of application No. 09/479,827, filed on Jan. 7, 2000, now Pat. No. 6,375,649, which is a division of application No. 08/930,335, filed on Dec. 22, 1997, now Pat. No. 6,436,069.

(51) Int. Cl.$^7$ .................................................. A61K 9/22
(52) U.S. Cl. ...................... 604/891.1; 604/107; 604/131; 604/151
(58) Field of Search ................................. 604/131–136, 604/151–153, 890.1, 891.1, 65–67, 19, 140, 141, 207, 212, 214, 216, 246, 104–109; 606/190, 191, 198

(56) References Cited

U.S. PATENT DOCUMENTS

| | | | | |
|---|---|---|---|---|
| 3,656,483 A | * | 4/1972 | Rudel | 604/285 |
| 3,811,443 A | * | 5/1974 | Dickinson et al. | 600/35 |
| 4,091,807 A | * | 5/1978 | Dickinson et al. | 128/898 |
| 4,251,506 A | * | 2/1981 | Laby | 424/438 |
| 4,258,711 A | | 3/1981 | Tucker et al. | 128/207.19 |
| 4,265,241 A | * | 5/1981 | Portner et al. | 604/131 |
| 4,312,347 A | * | 1/1982 | Magoon et al. | 604/891.1 |
| 4,360,007 A | | 11/1982 | Levy et al. | 128/1 R |
| 4,443,218 A | | 4/1984 | DeCant, Jr. et al. | 604/67 |
| 4,675,006 A | | 6/1987 | Hrushesky | 604/180 |
| 4,677,967 A | * | 7/1987 | Zartman | 128/830 |
| 4,714,462 A | | 12/1987 | DiDomenico | 604/67 |
| 4,871,351 A | | 10/1989 | Feingold | 604/66 |
| 4,883,467 A | | 11/1989 | Franetzki et al. | 604/152 |
| 4,944,659 A | | 7/1990 | Labbe et al. | 417/322 |
| 5,059,175 A | | 10/1991 | Hanover et al. | 604/891.1 |
| 5,318,557 A | * | 6/1994 | Gross | 604/891.1 |
| 5,328,460 A | | 7/1994 | Lord et al. | 604/67 |
| 6,375,649 B1 | * | 4/2002 | Jellie | 604/890.1 |
| 6,500,168 B1 | * | 12/2002 | Jellie | 604/890.1 |

FOREIGN PATENT DOCUMENTS

| | | | |
|---|---|---|---|
| EP | 0 079 724 | 5/1983 | 424/457 |
| EP | 0 134 614 | 3/1985 | F04B/43/14 |
| EP | 0 338 094 | 10/1989 | A61D/7/00 |
| EP | 0 387 439 | 9/1990 | A61M/5/14 |

* cited by examiner

Primary Examiner—Brian L. Casler
Assistant Examiner—Jennifer Maynard
(74) Attorney, Agent, or Firm—Darby & Darby

(57) ABSTRACT

According to one aspect of the present invention there is provided a substance delivery device (1) capable of insertion into a body cavity of an animal, including delivery apparatus (11) capable of actively being controlled to deliver a substance to an outlet, and retention apparatus (2, 3) capable of retaining the substance delivery device within the body cavity of an animal. In one embodiment, a microprocessor (18) can be remotely programmed to enable control over the delivery device after it is placed in the animal. The microprocessor (18) can also communicate with an external device to enable the operation of the delivery device to be determined. The invention may also include sensors to monitor the environment around the delivery device, to determine when a substance sod be delivered into the body.

20 Claims, 20 Drawing Sheets

SUBSTANCE DELIVERY DEVICE

RELATED APPLICATIONS

This is a division of application Ser. No. 09/479,827, filed Jan. 7, 2000, now U.S. Pat. No. 6,375,649, which is a division of application Ser. No. 08/930,335, filed Dec. 22, 1997, now U.S. Pat No. 6,436,069. Each of these prior applications is hereby incorporated herein by reference, in its entirety.

TECHNICAL FIELD

This invention relates to a substance delivery device which incorporates a controlled delivery apparatus and retention apparatus for said substance delivery device.

Reference throughout this specification shall be made to the substance delivery device as being for the introduction of substances within a body cavity, for example such as intravaginal, intraruminal devices and the like for domestic animals, such as cows. It should be appreciated however, that the principles of the present invention can apply to far wider applications than this and can be used with respect to delivery devices where some control is required.

In particular, it is envisaged that the retention apparatus will enable the substance delivery device to be most commonly used in situations where said device, capable of insertion into a passage or body cavity of an animal, is required to be retained in said passage or body cavity. Such passages or body cavities are generally associated with the reproductive or digestive systems of an animal, and include the vagina, uterus, stomach, rumen, and so forth. Such devices are inserted into an animal's body cavity where control of parasites, nutrition, reproduction, growth, and so forth are desired, and where this control is effected through chemical and/or hormonal intervention.

However, the present invention could have applications outside this field. Accordingly, these delivery devices may not necessarily be within the body of animals or humans, but may interact with other environments such as horticultural, industrial, domestic and so forth.

BACKGROUND ART

Commonly, substance delivery devices inserted into a living animal for dispensing substances to the animal also employ retention apparatus. Accordingly, a range of retention apparata exist for retaining the substance delivery device within a passage or body cavity of an animal.

Some systems commonly used for retaining delivery devices capable of being inserted into a body cavity of an animal, incorporate a compressible helica coil, such as in U.S. Pat. Nos. 228,382 and 190,350. The compressible coil is frequently capable of returning to the required shape after the device has been inserted into the animal's body cavity.

However, such coils rely on the overall bulk of the coil to retain the coil within the body cavity of an animal. Accordingly, the bulkiness of the coil may impede the flow of body secretions which may not be desirable. An unimpeded flow of body secretions is necessary for the normal biological functioning of the animal. Such body secretions include mucus, where such a device is used intravaginally.

In addition, the coil is typically capable of expanding and pressing against a considerable area of the wall of a body cavity of an animal, to the extent that it may be too bulky to pass back through passages leading into or out of the body cavity. Accordingly, when the functional utility of the device has been exhausted, removal of the device may be difficult.

Other systems commonly employed for retaining devices within the body cavity of an animal have incorporated a number of lobes, similar to those of U.S. Pat. No. 193,976 and U.S. Pat. No. 200,564. These lobes are often flexible enough to fold over onto each other for insertion into a body cavity of an animal and then spring open after the device is inside the animal. Frequently, the lobes perform a dual purpose of retaining the device within an animal's body cavity and of releasing an active ingredient, often impregnated into the lobe or in the coating around the lobe, into the animal's body cavity. Accordingly, the lobes may have a substantial, even rippled, surface area to ensure that sufficient active ingredient is available to perform the required function. In addition, the lobes are often specifically designed to provide a large surface area to enable the animal's body fluids to act on those surfaces to leach out active ingredients contained within the lobes.

However, the surface area of these devices is again capable of impeding the flow of body secretions. In addition, the natural elasticity of the lobes enables the lobes to be folded over onto each other to enable the device to be inserted into and removed from the animal's body cavity. However, an operator may be required to manually hold the lobes in the folded orientation, during insertion of the device into the animal's body cavity.

Further systems incorporate hinged legs or branched members, as in U.S. Pat. Nos. 215,635 and 230,023, which may extend from one or both ends of the body of a device inserted into the body cavity of an animal. Again, these legs or members, as well as the body of the device, are typically impregnated with active ingredients required to be dispensed into the animal. Accordingly, it is desirable that the legs or members add to the overall surface area of the device to enable the active ingredients to be more efficiently leached from the device and into the animal. Again, the common problem associated with such devices and retention systems for these devices, is that initially the increased surface area may impede the flow of the animal's internal body secretions. Particularly, the flow of mucus in the vagina of the animal.

However, with time, erosion of the polymer layers which contain the active ingredients, effectively reduces the surface area, overall size, and overall weight of the device. A problem is therefore that as the device gets smaller and lighter it does not have the same retentive ability.

In addition, such systems typically require an applicator, such as those described in U.S. Pat. Nos. 215,483 and 207,341. These applicators hold the legs or members into a required position to enable the device and the retention apparatus to be inserted into the animal's body cavity.

Often the applicators are complex or bulky structures, and are separate from the devices which they are capable of inserting. Inclusion of an applicator with the device may increase the costs of manufacture, and require insertion of the device into the applicator thereby extending the time associated with inserting devices into the animals.

Yet other systems may incorporate a number of distensible ribs, such as in U.S. Pat. No. 173,926. The ribs are capable of being distended into a possible retaining position by the action of a plunger system. When the plunger system is released the distensible ribs return to the undistended position for withdrawal. However, these devices are typically used for single applications of pharmaceutical formulations into the body cavity of an animal and are not intended to, nor are suitable for, retaining device over longer periods. The bulkiness of the plunger system, if left attached to the device could be a source of discomfort to the animal; the distensible ribs are typically unsuited to retaining a device in a larger body cavity; and the surface area of the ribs would impede the body's flow of secretions.

Yet other retention devices may be of sufficient dimensions to be retained in the body cavity of an animal by relying on muscle tension around the retention device. Such devices are typically used as intra-vaginal contraceptive devices for animals, such as in U.S. Pat. No. 173,808. However, the dimensions of the retention device may prevent penile insertion during attempted intermission by the male animal, and for impede flows of body secretions, particularly vaginal mucus.

Accordingly, it would be desirable if the retention apparatus of a substance delivery device enabled the delivery device to be easily inserted and removed, yet was reliably retained for required periods, and did not impede flow of body secretions or adversely affect normal functioning by its mere physical presence.

Similarly, a range of delivery apparata for delivering substances are well known, and have broad application.

Many incorporate pumps and are used to dispense common substances such as petrol and air. Some delivery apparata are used inside a living animal to dispense useful substances such as chemicals or drugs.

For example, there are a number of delivery apparata known that introduce substances such as hormones intravaginally to cows. The purpose of such apparata is to promote with some accuracy the onset of oestrus. This enables the farmer to artificially inseminate the cows at a time when they are most fertile.

For example, New Zealand Patent No. 228382 discloses such a delivery apparatus. The device disclosed consists of a helical coil made up of a number of segments. These segments contain useful substances which are either impregnated into or coated onto.

The substance to be administered to the animal is gradually released from the segments of the apparatus over a period of time by the action of body fluids. Accordingly, such apparatus relies on the natural processes of diffusion, dissolution, or osmosis to dispense the substance.

Various other delivery apparata as described in New Zealand Patent Nos. 207341, 200564 and 215635 all release drugs into the body cavity passively, as consequence of the action of body fluids.

However, when controlling oestrus in animals for example, different hormones or concentrations need to be released into the animal's body at different times. To effect this, previous delivery apparata have had a number of layers, perhaps with different thicknesses, containing both passive and active substances. These enter the body by the diffusion, dissolution or osmosis, all these processes being dependent upon the body fluids surrounding the substance delivery device or delivery apparata within the device.

For example, it may be desirable to introduce into the body for a period of ten days a certain hormone, then no hormone for another ten days and then introduce another hormone for another period of time. The delivery device could have layers of thicknesses proportional to the time it is estimated that these layers will take to dissolve into the body system.

Unfortunately, there are problems associated with these devices incorporating such delivery apparata. All of these devices are passive devices dependent upon the body fluids surrounding them for the introduction of the active substances into the body.

However, the rate of introduction of these substances is dependent upon a number of factors such as the temperature, mucus concentration, salt concentration, kinetic action and so forth of the body fluids. These factors are variable from animal to animal which leads to variable timing and concentration of the substances being introduced into the body.

Further, with the substances being exposed to the body's environment, it is possible for the layers to be chipped and a completely inappropriate substance introduced into the body at the wrong time. Hence, such systems tend to restrict themselves to delivery of a single active material or if more than one, the second material is introduced at the start.

In addition, once these delivery devices are inserted into an animal, the delivery of substance into the animal cannot be controlled as it is totally dependent upon the environment that it is in.

The ability to control the amount and timing of dispensation of a substance with any degree of accuracy is difficult, as there is a dependence upon the external environment to provide the conditions necessary for dispensation to occur, with the conditions determining the volume and rate of dispensation. Accordingly, delivery apparatus reliant on osmosis, diffusion, and dissolution all suffer from inaccuracy in dispensing and inherently have little timing precision.

Alternately, conventional pumps are often large and complicated. They contain moving parts, complex valve systems, are usually difficult to operate with any degree of accuracy, and are often not suitable for insertion into an animal's body. Further, conventional pumps often require regular maintenance.

It would therefore be desirable if there could be provided a delivery device which was small and simple, contained no complex parts, was maintenance free, and which could be used in animal's bodies or other such environments.

It would also be desirable if there could be provided a device which included delivery apparatus capable of being accurately operated to deliver substances into an animal in precise concentrations and with precise timing, and where such a apparatus could operate independently of the environment, or the apparatus could release substances into the environment only when the environment was ideal.

In addition, it would be desirable if there could be effected some control over the delivery apparatus after the device is placed in the animal, and/or if there was some way of determining what was happening within the animal with respect to the operation of the device and associated delivery apparatus.

It is an object of the present invention to address the above problems or at least to provide the public with a useful choice.

Further objects and advantages of the present invention will now be discussed by way of example only.

DISCLOSURE OF INVENTION

According to one aspect of the present invention there is provided a substance deliver device capable of insertion into a body cavity of an animal, including delivery apparatus capable of actively being controlled to deliver a substance to an outlet, and retention apparatus capable of retaining the substance delivery device within the body cavity of an animal.

In preferred embodiments of the present invention the body of the substance delivery device is configured to include a chamber capable of receiving delivery apparatus and associated controlling apparatus, and the attachment and/or operational means of the retention apparatus.

The body of the substance delivery device may also be so configured to improve the ease with which the substance delivery device is inserted into and withdrawn from the body of an animal. Accordingly, the body of the substance delivery device may be substantially circular in cross-section, be tapered along its length, may include a thread or so forth for pulling the device out of the animal's body, and so forth.

In preferred embodiments of the present invention the retention apparatus is attached to the body of the substance delivery device which is capable of being inserted into and required to be retained in a passage or body cavity of an animal.

For ease of reference the substance delivery device capable of insertion into a body cavity or passage of an animal shall now be referred to simply as the device, although it should be appreciated that this term is not intended to be seen as limiting.

According to another aspect of the present invention there is provided a method for retaining a substance delivery device substantially as described above within a body cavity of an animal into which the substance delivery device is inserted, via use of retention apparatus.

In preferred embodiments of the present invention the retention apparatus is attached to the device capable of being inserted into the vagina of an animal. Although, in other embodiments of the present invention the retention apparatus may also be attached to a device capable of being inserted into other body cavities or passages of an animal.

In preferred embodiment of the present invention the retention apparatus is an integral part of the body of a device to which the retention apparatus is attached. Having the retention apparatus as an integral part of a device obviates problems of having to attach the retention apparatus as a separate portion at a later stage of construction. Further, it enables the same material to be used for both the body of the device and the retention apparatus. Therefore, where the retention apparatus is moulded as an integral part of the body of a device, the expense and time associated with construction of the retention apparatus and device may be reduced.

However, in other embodiments of the present invention the retention apparatus may be a separate portion. Having a retention apparatus which is a separate portion, enables the retention apparatus to be attached to a device at a later stage of construction; enables the retention apparatus to be made of different materials to the body of the device; may enable a particular form of retention apparatus to be used on a number of different devices; or enables one device to be fitted with any one of a range of retention apparatus depending on the body cavity into which the device is to be inserted.

According to another aspect of the present invention there is provided a substance delivery device substantially as described above wherein the retention apparatus is located at at least one end of the substance delivery device.

In preferred embodiments of the present invention the retention apparatus is located towards at least one end of the device to which the retention apparatus is attached. Having the retention apparatus attached to at least one end of the device being retained, obviates problems associated with the retention apparatus impeding the flow of body secretions, such as intravaginal mucus, which may occur where there are retention apparatus located at a number of points along the device.

However, in some embodiments of the present invention the retention apparatus may be located at either end, or at any point along the body of the device. This may be particularly useful in situations where the flow of internal body secretions is not adversely affected by the retention apparatus. In addition, positioning the retention apparatus at other locations may be required where the strength of internal peristaltic waves within an animal's body cavity is such that a number of retention apparatus, or a need for retention apparatus located in particular positions along the body of the device is required to enable the device to be more reliably retained within the animal's body cavity.

In preferred embodiments of the present invention the retention apparatus is located towards the leading end of the device to which the retention apparatus is attached. Locating the retention apparatus at the leading end of the device is a configuration which is frequently adapted and found to be practically suited for insertion of the device into or through a passage leading to an animal's body cavity, such as the vagina.

In some embodiments of the present invention the retention apparatus may be located at the trailing end, each end, or at any point along the body of the device to which the retention apparatus is attached, depending on the method of insertion of the device, and the passage or body cavity into which the device is to be attached.

According to another aspect of the present invention there is provided a substance delivery device substantially as described above wherein the retention apparatus capable of insertion into a body cavity of an animal includes, multiple arms capable of retaining said device within said body cavity of an animal, characterised in that the arms are substantially flexible.

In preferred embodiments of the present invention the retention apparatus includes multiple arms. Having multiple arms increases the potential points of contact between the retention apparatus and the walls of the animal's body cavity, into which the retention apparatus has been inserted. Increased points of contact contribute to the ability of the retention apparatus to remain in the appropriate passage or body cavity, without being dislodged by the animal's internal peristaltic movements.

In some embodiments of the present invention the number of arms of the retention apparatus may vary, depending on the passage or body cavity into which the device is to be inserted and any corresponding peristaltic movements within the passage or body cavity.

In preferred embodiments of the present invention the retention apparatus is made of polymer plastic materials, such as Hytrel™. The flexibility of this material is an important consideration, as it is able to be compressed or subjected to tensile stress without the shape becoming distorted. The ability of this polymer plastic material to revert to its original shape is known as "compressive creep modulus". In addition, this material is durable, it does not crack when bent, has smooth surfaces after moulding which seems to decrease risks of contamination to the animal, is capable of being moulded, capable of being sterilised for hygienic reasons, is lightweight, chemically resistant, can withstand wet environments, and is economical.

However, in other embodiments of the present invention the retention apparatus may be made of other materials, such as rubber, or a material which is capable of degrading after a known period of time. The use of a degradable material for the retention apparatus could be used to enable devices for which the functional utility has been exhausted, to be more easily removed from a body cavity or passage of an animal.

In preferred embodiments of the present invention the arms of the retention apparatus are substantially flexible.

The substantial flexibility of the arms of the retention apparatus enables the arms to flex in both a vertical plane and a horizontal plane in response to changes in the size of the animal's body cavity due to internal peristaltic waves. Thus the arms are capable of remaining in contact with the internal walls of the animal's body cavity without the arms of the retention apparatus snapping or becoming permanently bent. Accordingly, after the peristaltic wave has passed, the substantially flexible arms are capable of returning to their original shape.

In other embodiments of the present invention the degree of flexibility of the arms of the retention apparatus may be varied in response to the conditions existing within the body cavity into which the retention apparatus is to be inserted.

According to another aspect of the present invention there is provided a substance delivery device substantially as described above wherein the arms of the retention apparatus include a body portion and a distal portion.

In preferred embodiments of the present invention each arm of the retention apparatus includes a body portion and a distal portion.

For ease of reference the body portion and the distal portion of the arms of the retention apparatus shall now be referred to as the shaft and the tip, respectively. Although, it should be appreciated that these terms are not intended to be limiting.

In preferred embodiments of the present invention the shaft of each arm is substantially elongate. Substantially elongate shafts enable the retention apparatus to engage with walls of a body cavity of an animal. Engagement of the arms of the retention apparatus with the walls of the animal's body cavity enables the arms of the retention apparatus to maintain contact with the walls of the body cavity throughout changes to the dimensions of the body cavity in response to peristaltic waves moving through the musculature of the walls of the body cavity. Those peristaltic waves otherwise cause the retention apparatus to be dislodged.

In other embodiments of the present invention the shafts of the arms of the retention apparatus may be extendible telescopically. Telescopic extension of the arms may enable the arms of the retention apparatus to be adapted to suit a range of sizes of body cavities or passages into which the retention apparatus may be inserted.

In preferred embodiments of the present invention the shaft of each arm of the retention apparatus has a substantially limited cross-sectional dimension.

For ease of reference the substantially limited cross-sectional feature of the shaft of each arm of the retention apparatus shall now be referred to as thin, although the use of this term is not intended to be limiting.

A thin shaft enables the retention apparatus to have multiple arms, which enhance the retention capability of the device without the shafts of the arms impeding the flow of body secretions. An unimpeded flow of body secretions is necessary for the normal biological functioning of an animal's reproductive system, digestive system, and so forth.

In some embodiments of the present invention however, the shaft of each arm of the retention apparatus may be thicker, or the arms may have varying cross-sectional dimensions, depending on the strength of the peristaltic waves in the body cavities into which the retention apparatus is inserted and depending on the types of body secretions present in the different body cavities of an animal.

In preferred embodiments of the present invention the shaft of each arm of the retention apparatus is substantially circular. Having a substantially circular shaft avoids the possibility of sharp edges causing irritation of the interior walls of the animal's body cavity. In addition, substantially circular, thin shafts are inherently stronger than thin, flat shafts or lobes, for example, and are more capable of withstanding the forces of the internal peristaltic waves within the animal's body cavity. Further, a rounded surface is less likely to impede flows of body secretions to the same extent that a flat surface might.

However, in other embodiments of the present invention, the shafts may be flat, V-shaped, U-shaped, hexagonal, and so forth, depending on the internal conditions of the body cavity into which the retention apparatus is inserted, and the corresponding shaft strength required.

In preferred embodiments of the present invention the arms of the retention apparatus are substantially straight. Straight arms may enable the arms of the retention apparatus to be more compactly aligned with the body of the device, for easier insertion into an animal's body cavity,. Although, in other embodiments the arms may be curved, undulating, and so forth, to meet the particular needs associated with different body cavities.

According to another aspect of the present invention there is provided a substance delivery device substantially as described above wherein the distal portions of the arms of the retention apparatus have a substantially greater cross-section than the body portion.

In preferred embodiments of the present invention the tip of each arm of the retention apparatus has a substantially greater cross-sectional dimensions than the shaft of the arm. The greater cross-sectional dimension of the tip provides a greater surface area for the arm to contact the internal walls of the animal's body cavity, than would be available if the tip retained the same cross-sectional dimension of the shaft. The greater the contact with the body cavity walls, the better the retention of the apparatus, and of the device to which the retention apparatus may be attached, within the animal's body cavity. In addition, the greater cross-sectional dimension of the tip is capable of reducing the likelihood of injury to the animal, that might otherwise occur where a thin shaft contacts the soft tissue.

However, in other embodiments of the present invention, where it is necessary for the shaft of the arm of the retention apparatus to be thicker to compensate for stronger internal peristaltic waves of the animal's body cavity, the tip and the shaft of the arm of the retention apparatus may have the same cross-sectional dimension. In addition, in other embodiments only some of the tips of the arms of the retention apparatus may have greater cross-sectional dimensions, depending on the number of arms of the retention apparatus, and/or body cavity into which the retention apparatus is inserted.

In preferred embodiments of the present invention the tip of each arm of the retention apparatus is substantially bulbous. The rounded surface of the substantially bulbous tip is capable of increasing the surface area of contact between the retention apparatus and the internal walls of the animal's body cavity, thereby improving the potential retentive ability of the retention apparatus. In addition, the rounded edges of the bulbous tip obviates problems of irritation of, or injury to, the internal walls of the animal's body cavity, which may occur with tips that have sharper edges.

In other embodiments of the present invention the tip of each or any m may be flattened so as to be substantially perpendicular to the shaft, or may be substantially tapered, and so forth, depending on the internal structure of the body cavity into which the retention apparatus is inserted.

According to another aspect of the present invention there is provided a substance delivery device substantially as described above wherein the arms of the retention apparatus are capable of being substantially aligned with each other and the longitudinal axis of the body of the substance delivery device to which the retention apparatus is attached, for ready insertion or withdrawal of said substance delivery device into a body cavity of an animal.

According to another aspect of the present invention there is provided a substance delivery device substantially as described above wherein the arms of the retention apparatus are capable of being aligned substantially parallel to the body of the substance delivery device to which the retention apparatus is attached, ready for insertion or withdrawal of said substance delivery device into or from a body cavity of an animal.

According to another aspect of the present invention there is provided a method of inserting into and withdrawing from a body cavity of an animal, a substance delivery device substantially as described above.

In one preferred embodiment of the present invention the arms of the retention apparatus are capable of being aligned substantially parallel to the body of a device required to be inserted into an animal's body cavity. Alignment of the arms substantially parallel to the body of the device enables the device and retention apparatus to be more easily inserted into an animal's body cavity through a passage, or be inserted for retention within a passage, such as the vagina. When the arms of the retention apparatus are on the leading edge of the device, pressure of the walls and the opening of a passage way or of an animal's body cavity may be relied on to maintain the arms in a parallel arrangement with the body of the device. Insertion of the retention apparatus and the device configured in this way, obviates problems of having to hold the arms of the retention device together to avoid the arms splaying out during insertion, as would be required if the arms protruded forward of the device.

Alternatively, an applicator or even the packaging of the device, may be used to align the arms parallel to the body of the device.

In another preferred embodiment of the present invention the arms of the retention apparatus are capable of being substantially aligned with each other and the longitudinal axis of the body of the device to which they are attached. Again, this alignment of the arms of the retention apparatus with the body of the device allows the device and retention apparatus to be more easily inserted through or into a passage way or into an animal's body cavity. The retention apparatus may rely on some initial pressure applied by an operator's hands to maintain alignment of the arms of the retention apparatus prior to insertion into the animal. As insertion commences, the pressure of the walls of the passage way or opening of the animal's body cavity will maintain the arms in a longitudinally aligned position.

Alternatively, where the retention apparatus and device are to be specifically inserted into a passage such as the vagina of an animal, a removable band may maintain the longitudinal alignment of the arms of the retention apparatus. On insertion of the retention apparatus and device, the removable band may roll back down the arms of the retention apparatus to rest on a portion of the body of the device.

In addition, an applicator may be used to align the arms with each other along the longitudinal axis of the body. The applicator may be specifically designed for use with the retention apparatus and device required to be retained in an animal's body cavity, or may merely be the packaging in which the retention apparatus and device are supplied.

In preferred embodiments of the present invention the retention apparatus is capable of being removed from the passage or body cavity of an animal. Once the functional utility of the device to which the retention apparatus is attached has been exhausted, the device may be withdrawn assisted by the pressure exerted by the walls of the passage or the opening to the body cavity. The pressure, in combination with the substantial flexibility of the arms of the retention apparatus, enables the arms to become aligned with each other and to the longitudinal axis of the body of the device, or aligned substantially parallel to the body of the device. The device may then be withdrawn with minimum discomfort to the animal.

According to another aspect of the present invention there is provided a substance delivery device substantially as described above wherein the arms of the retention apparatus are capable of being extended for retaining the substance delivery device within a body cavity of an animal into which said device is inserted.

According to another aspect of the present invention there is provided a substance delivery device substantially as described above wherein the arms of the retention apparatus are operable between either an aligned inserting or an aligned withdrawal position and an extended retaining position.

According to another aspect of the present invention there is provided a method of operating multiple arms of retention apparatus of a substance delivery device substantially as described above, between an aligned inserting configuration and an extended retaining configuration.

In preferred embodiments of the present invention the arms of the retention apparatus are capable of being operable between an aligned inserting position and an extended retaining position.

In a preferred embodiment of the present invention the end of the shaft opposite the tip of each arm of the retention apparatus is moulded to the body of the device form a substantially resilient hinge at that junction between the arm of the retention apparatus and the body of the device. The resilient hinge enables the arms of the retention apparatus to be more closely aligned to the body of the device, for insertion of the retention apparatus into a body cavity or passage of an animal. In addition, after insertion, the substantially resilient hinge enables the arms of the retention apparatus, in conjunction with locking apparatus, to assume the extended retaining position of the retention apparatus.

In some embodiments of the present invention other hinges known in the prior art may be adapted for use with the present retention apparatus.

In another preferred embodiment each arm is completely moulded onto the body of a device. In this configuration of the retention apparatus the substantially flexible arms of the retention apparatus are capable of being flexed to enable the arms to be aligned for insertion of the retention apparatus into an animal's body cavity. After insertion, the substantially flexible arms of the retention apparatus are able to assume their extended retaining position.

According to another aspect of the present invention there is provided a substance delivery device substantially as described above wherein the arms of the retention apparatus are capable of being locked in an extended retaining position.

According to another aspect of the present invention there is provided locking apparatus capable of locking the arms of the retention apparatus of a substance delivery device, substantially as described, above in a retaining position.

According to a further aspect of the present invention there is provided locking apparatus for retention apparatus of a substance delivery device substantially as described above wherein said locking apparatus includes either one or both of biasing apparatus and plunging apparatus.

In preferred embodiments of the present invention the arms of the retention apparatus are capable of being maintained in an extended retaining position by the action of locking apparatus.

In preferred embodiments of the present invention the locking apparatus includes either or both of biasing apparatus and plunger apparatus. However, a number of locking apparatus exists in the prior art and may be adapted for use with the retention apparatus.

For ease of reference the biasing apparatus and plunger apparatus shall now be referred to as a spring-loaded collar and plunger apparatus, respectively, although it should be appreciated that these terms are not to be seen as limiting.

In preferred embodiments of the present invention the spring-loaded collar is capable of operating between a biased position and an unbiased position. When the retention apparatus is in its inserting position the spring-loaded collar is cocked in its biasing position by the alignment of the arms of the retention apparatus. At a point during the process of insertion, removal of the pressure required to align the arms of the retention apparatus with the device, enables the arms to move towards the extended retaining position. This initial movement of the unrestrained arms causes the spring-loaded collar to be activated.

On activation the spring-loaded collar moves in a direction towards the junction where the arms of the retention apparatus meet the device, and in a direction which is substantially in line with the longitudinal axis of the device to which the retention apparatus is attached. In embodiments which includes a plunger, the plunger is open when the arms are in the inserting position, when the spring-loaded collar is activated the plunger is closed. Accordingly, the arms of the retention apparatus are thereby held in the extended retaining position by either or both of the spring-loaded collar and the plunger apparatus.

In preferred embodiments of the present invention the spring-loaded collar and plunger are incorporated into the leading edge of the device capable of insertion into an animal's body cavity. However, in other embodiments, the spring-loaded collar and plunger may be located at the trailing end of the device. Alternatively, the spring-loaded collar may be located at points along the body of the device, in conjunction with the retention apparatus located at that location.

According to another aspect of the present invention there is provided a substance delivery-device substantially as described above wherein the arms of the retaining apparatus occupy a plane substantially perpendicular to the body of the substance deliver device inserted into a body cavity of an animal when locked in an extended retaining position.

According to another aspect of the present invention there is provided retention apparatus substantially as described above wherein the arms of the retention apparatus attain a substantially radial arrangement when said arms are locked in an extended retaining position.

In preferred embodiments of the present invention the arras of the retention apparatus are locked into a substantially radial arrangement around the portion of the body of the device to which the retention apparatus is attached, when the arms are in the extended retaining position.

In preferred embodiments of the present invention the spring-loaded collar of the retention apparatus operates to lock the arms of the retention apparatus in a plane substantially perpendicular to the body of the device inserted into the body cavity of an animal. This arrangement enables the device, to which the retention apparatus is attached, to operate unimpeded by the walls of the body cavity into which the device has been inserted. Where such devices release an active ingredient, the retention apparatus maintains the device in a position whereby the active ingredient released from the body of the device, may be free to mix with appropriate bodily secretions, or be absorbed through the walls of the body cavity into which the device has been inserted.

According to a further aspect of the present invention there is provided delivery apparatus for delivering a substance to an outlet of a substance delivery device substantially as described above wherein the delivery apparatus includes at least one conduit capable of containing the substance, at least one pressure device capable of applying pressure to the conduit, and valve means characterised by application of pressure by the pressure device and activation of the valve means causing the substance within the conduit to move along the conduit to the outlet.

According to a further aspect of the present invention there is provided a method for delivering a substance to an outlet of a substance delivery device substantially as described above including at least one conduit capable of containing the substance, at least one pressure device capable of applying pressure to the conduit and valve means, characterised by the steps of applying pressure to the conduit and valve means, causing the substance within the conduit to move-along the conduit to the outlet.

The delivery apparatus itself may take many forms as long as it can be controlled to actively deliver the substance. The mechanism by which the delivery apparatus actively introduces the substance is via a pressure device, and/or valve means.

The term substance used in this specification shall mean any substance including liquid or gas.

The term pressure used in this specification shall mean the application of force, and the term pressure device shall include any mechanism used to apply force (such as a pump or spring and plunger system).

The term conduit used in this specification shall mean any apparatus capable of conveying a substance and may in some instances be a reservoir.

The flexible conduit may be divided into two ends. One end, hereinafter referred to as the inlet, is connected to the substance source. The opposite end, hereinafter referred to as the outlet, is connected to the outlet of the delivery apparatus, of the substance delivery device.

The term valve used in this specification shall mean any means, including automatic or other device, used to apply force to, or capable of conveying, a substance from the conduit to the outlet. In some embodiments the valve means may be different from and/or replace one or all of alternate pressure devices.

The term armature used in this specification shall mean any apparatus of suitable material, capable of being treated, or capable of responding to a magnetic or other force field, and when placed in the vicinity of a magnet or other force, has its operational capability increased.

The term coil member used in this specification shall mean any apparatus capable of responding to an energy supply, such that a magnetic field, or other force field is created in the vicinity of the coil member.

In conventional substance delivery devices for use inside bodies or other such environments the substance is passively delivered by the natural process of osmosis, diffusion, or dissolution. The rate and volume of substance delivery are determined by the natural processes. Thus, the rate and volume of substance delivery cannot be controlled or varied by artificial means. It is believed that the pressure devices and/or valve means provide a means of actively delivering the substance. Active delivery of a substance provides a means of controlling the rate and volume of the substance delivered.

In one preferred embodiment the valve means is a metering valve system, which operates on a reversed magnetic polarity principle, and includes a moving and a fixed armature.

Preferably, the armatures are made from materials capable of being magnetised.

The metering valve system also preferably includes a coil member which is capable of being activated. On activation of the coil member, a solenoidal effect is produced which causes the moving armature to be attached to and seal against the stationary armature. Deactivation of the coil member enables the moving armature to move away from the fixed armature.

In preferred embodiments the structural configuration of the metering valve system creates a chamber within the conduit. Accordingly, movement of the moving armature towards and away from the fixed armature enables some of the substance which has passed into this chamber to move along the conduit to the outlet.

The metering valve system also preferably incorporates tension apparatus, such as a spring, to ensure that the valve system is able to reliably seal, when required.

According to another aspect of the present invention there is provided delivery apparatus for delivering a substance to an outlet of a substance delivery device substantially as described above wherein the delivery apparatus includes at least one flexible conduit capable of containing the substance, at least one pressure device capable of applying pressure to the flexible conduit at variable points along the conduit, characterised by the application of pressure by the pressure device causing the substance within the conduit to move along the conduit to the outlet According to a further aspect of the present invention there is provided a method for delivering a substance to an outlet of a substance delivery device substantially as described above, including at least one flexible conduit capable of containing the substance, at least one pressure device capable of applying pressure to the flexible conduit at variable points along the conduit characterised by the step of using the pressure device to apply pressure to the conduit causing the substance within the conduit to move along the conduit to the outlet.

According to a further aspect of the present invention there is provided a method of delivering a substance to a body characterised by the step of using delivery apparatus and/or method as previously described.

The action of the delivery apparatus in delivering the substance shall now be referred to as peristaltic.

While in one embodiment there may be one or two pressure devices, in another preferred embodiment there are three pressure devices.

In the alternative preferred embodiment the three pressure devices are positioned sequentially along flexible conduit.

The first pressure device may be located closest to the inlet. The second pressure device may be located between the first pressure device and the third pressure device. The third pressure device is located closest to the outlet.

When the first pressure device applies pressure to the conduit the substance is pushed along the flexible conduit by the application of pressure. The substance is moved as a consequence into the vicinity of the second pressure device. The pressure from the first pressure device remains applied. The second pressure device then applies pressure causing the substance to be moved further along the flexible conduit and into the vicinity of the third pressure device. The first pressure device may be released. The third pressure device may then apply pressure moving the substance towards the outlet. This sequence may be continued to move sufficient substance out of the delivery apparatus of the delivery device as required.

Releasing one pressure device after the next pressure device in the sequence has been applied prevents flow back and ensures that the flow of the substance towards the outlet continues.

The pressure devices may be controlled by any controlling mechanism such as a micro-processor.

The pressure devices which operate as described above are capable of controlling the flow of substance through the flexible conduit. Conventionally, conduits require valves to prevent back flow. The capability of the pressure devices to control the flow of substance removes any need for separate valves to prevent such back flow.

In some embodiments of the present invention the conduit may be greater in length and there may be two or more sets of three pressure devices.

According to a further aspect of the present invention there is provided a substance delivery device substantially as described above, wherein a delivery device for delivering a substance to an outlet including at least one flexible conduit capable of containing the substance, at least one pressure device capable of applying pressure to the flexible conduit at variable points along the conduit, characterised by the application of pressure by the pressure device causing the substance within the conduit to move along the conduit to the outlet, wherein the pressure device is composed of a piezo pump or a combination of piezo pump and any other type of pump.

Piezo pumps contain crystals move upon the application of electrical current. These can be quite small devices which can be controlled to a high degree of accuracy. As the operation of the piezo pump is dependent on current only, few moving parts are required and the construction is simple.

In preferred embodiments there are three piezo electric pumps, but there may be any number.

For ease of reference the pressure devices shall now also be referred to as pumps. However, it should he appreciated that use of this term is not intended to be limiting.

Piezo pumps are small in the preferred embodiment, having a diameter of 6.4 millimeters at their widest point and a length of 12 millimeters. Thus, piezo pumps are well suited to delivery devices where space is limited, such as inside bodies.

Piezo pumps are economical pressure devices which have a low power draw and therefore can be readily battery powered.

According to a further aspect of the present invention there is provided a means of utilising energy sources in the surrounding environment. The energy sources may include kinetic, chemical, or thermal energy.

It can be seen that the present invention has a number of advantages over the prior art.

The pressure devices are small, simple, and require little maintenance, and are thus suitable to pit inside bodies or other such environments.

According to another aspect of the present invention there is provided a method of introducing a substance into an animal from a substance delivery device substantially as described above, characterised by the step of controlling the operation of the delivery apparatus so that the substance is actively introduced into the animal.

The pump and/or valve means of the delivery apparatus may be controlled by a variety of means. In preferred embodiments, the means of control is a microprocessor. It should be appreciated however that other control mechanisms such as an 'ASIC' (Application Specific Integrated Circuit) may be used.

The advantages of having active control over the introduction of the substance is readily apparent. The pressure devices are actively operated by the controlling mechanism and thus the rate and volume of substance delivered may be controlled. Accordingly, active delivery means that there is greater control so that the precise concentration of the substance can be delivered at the precise time, independent of the environment surrounding the substance delivery device, or delivery apparatus.

The means by which the microprocessor can control this pump can vary. The pump may be powered by an energy source (perhaps a battery, an external source such as the animal's body, a magnetic field, a spring or the like) and the action of the microprocessor may be merely to connect or disconnect the pumps from the energy source.

Alternatively, the microprocessor may control the valve or valves which permit or prevent the flow of substance from the delivery apparatus, and substance delivery device.

In one embodiment of the present invention, the microprocessor may be programmed to control the release of varying doses of differing hormones into the animal at predetermined times, thus allowing for accurate determination of when oestrus occurs.

According to a further aspect of the present invention there is provided a method of controlling the deliver apparatus of a substance delivery device substantially as described previously characterised by the step of introducing predetermined amounts of substance at predetermined times into the body of an animal.

There are further advantages of having an active control delivery of substance to an animal. For example, there may be provided sensors which monitor the environment around the substance delivery device or delivery apparatus. The sensors may determine when the environment is ideal for the introduction of a substance into the body of the animal. This information may be then acted upon by the microprocessor to control the delivery apparatus to introduce those substances.

For example, the sensors could determine factors in the body fluid surrounding the substance delivery device and/or delivery apparatus, such as temperature, acidity. viscosity or even odour. These physiological indicators may in some instances be more accurate than a calendar date for determining when certain substances should be introduced into the animal. With active control, an accurate response to these physiological conditions is possible.

In some embodiments of the present invention the microprocessor may actually alter the size of the dose as well as the timing depending upon the environment the device is in.

In other embodiments of the present invention the action of the delivery apparatus may be remotely activated. For example, the device may remain inactive within the animal for a period of time until the farmer wishes to start the fertility cycle. At which stage, the farmer may have an external device to the animal which triggers the action of the delivery apparatus or wakes up the microprocessor. This external device may come in many forms, for example it may be a radio transmitter, an ultrasonic transmitter, a magnet and so forth.

In some embodiments of the present invention, remote programming of the microprocessor may be possible from outside the animal or at time of insertion.

In other embodiments of the present invention the microprocessor may be able to communicate to an external device. For example, the microprocessor may feed back data as to how much substance has been delivered, the temperature of the environment and so forth.

An appropriate microprocessor for use with the present invention is a four bit microprocessor or an 8 bit single chip microprocessor such as a pic 16c54 or Z8 or Motorola 6805.

It should be appreciated that although reference throughout this specification has been made to the use of the present invention as a substance delivery device or delivery apparatus for use within animals, the delivery apparatus, control mechanisms, and retention apparatus described may be used in substance delivery devices in other environments, particularly in environments which it is not possible to directly access the substance delivery device.

BRIEF DESCRIPTION OF DRAWINGS

Further aspects of the present invention will become apparent from the ensuing description which is given by way of example only and with reference to the accompanying drawings in which.

BEST MODES FOR CARRYING OUT THE INVENTION

Figure 1:
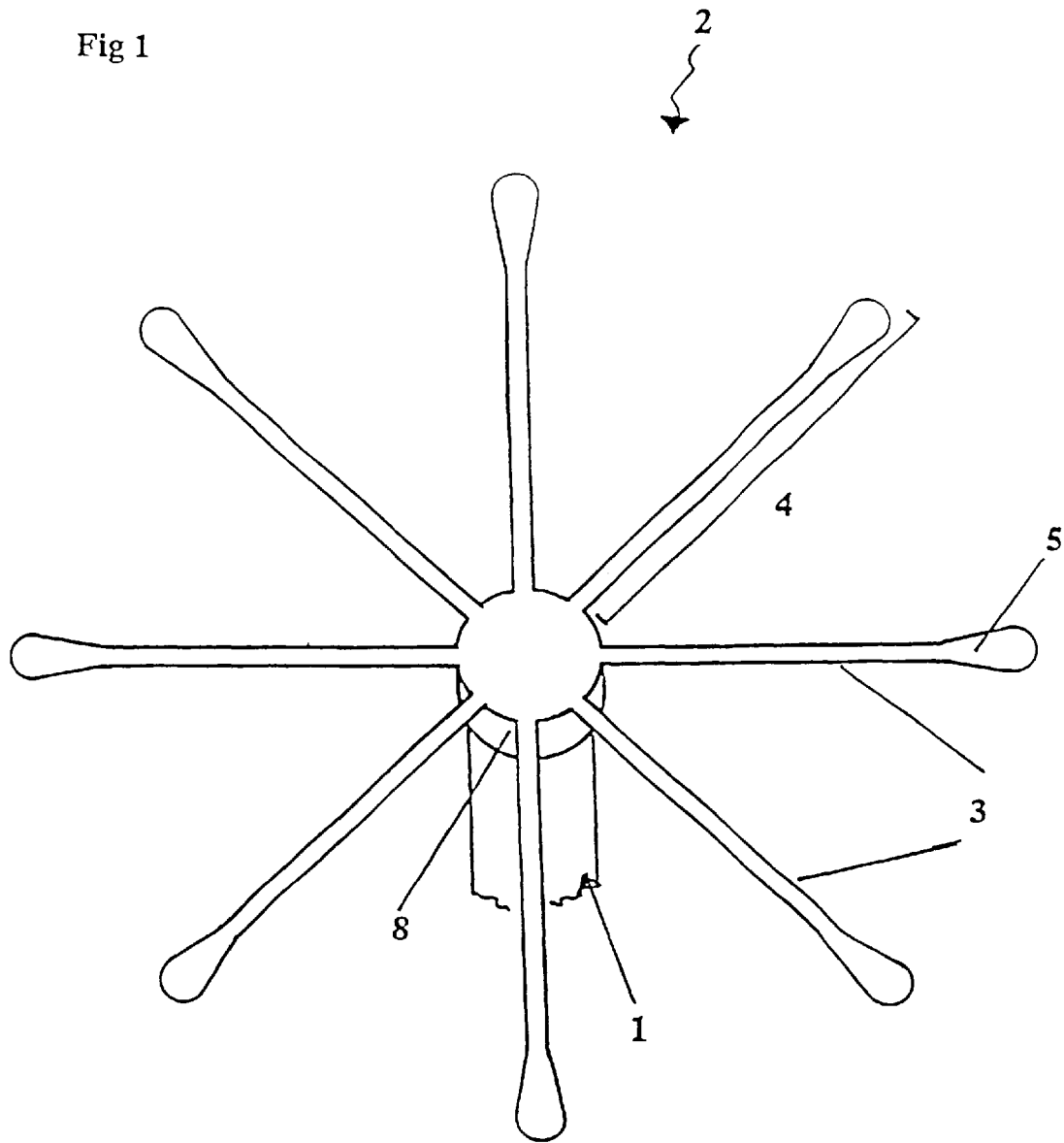
FIG. 1 is a diagrammatic perspective view of a retention apparatus in accordance with one embodiment of the present invention.

With reference to the diagrams by way of example only there is provided substance delivery device generally indicated by arrow 1. The substance delivery device 1 includes retention apparatus generally indicated by arrow 2. The substance delivery device 1 is capable of insertion into a body cavity or passage of an animal.

The retention apparatus 2 includes multiple arms 3 characterised in that the arms 3 are substantially flexible.

Figure 2:
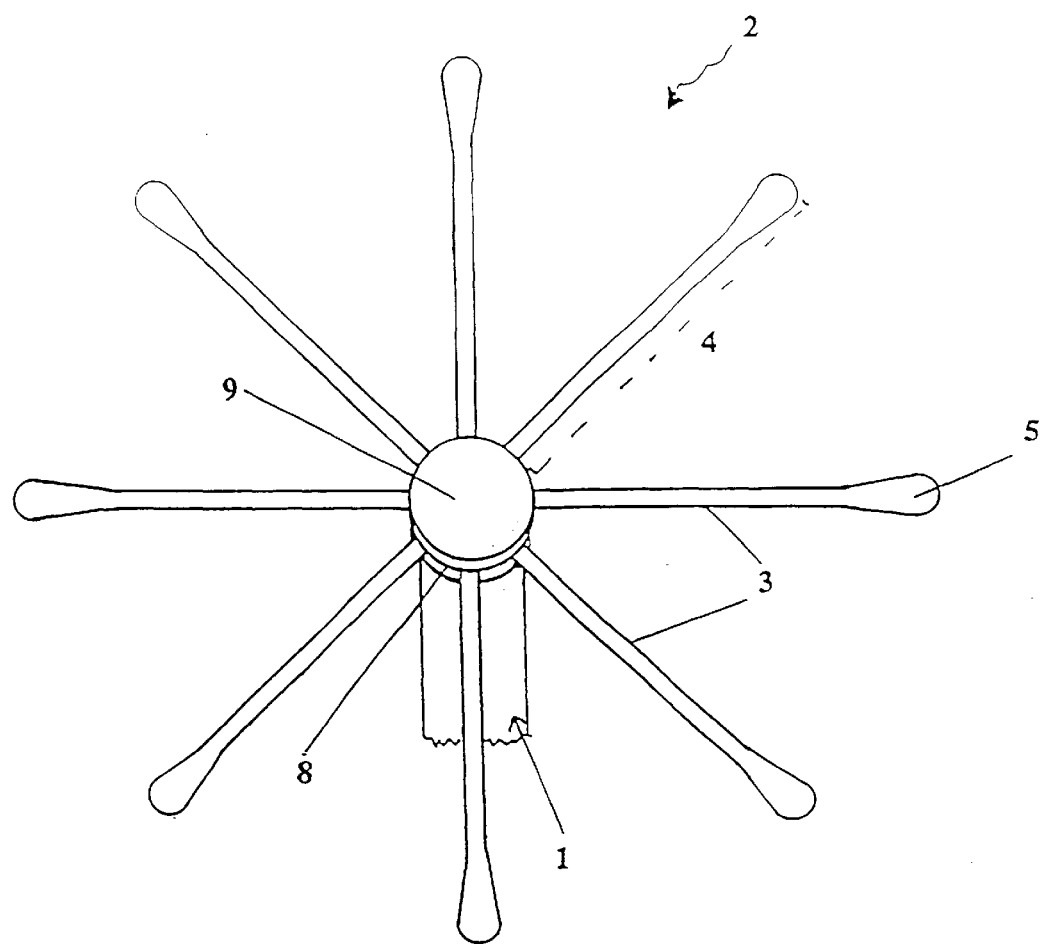
FIG. 2 is a diagrammatic perspective view of a retention apparatus in accordance with another embodiment of the present invention.
Figure 3:
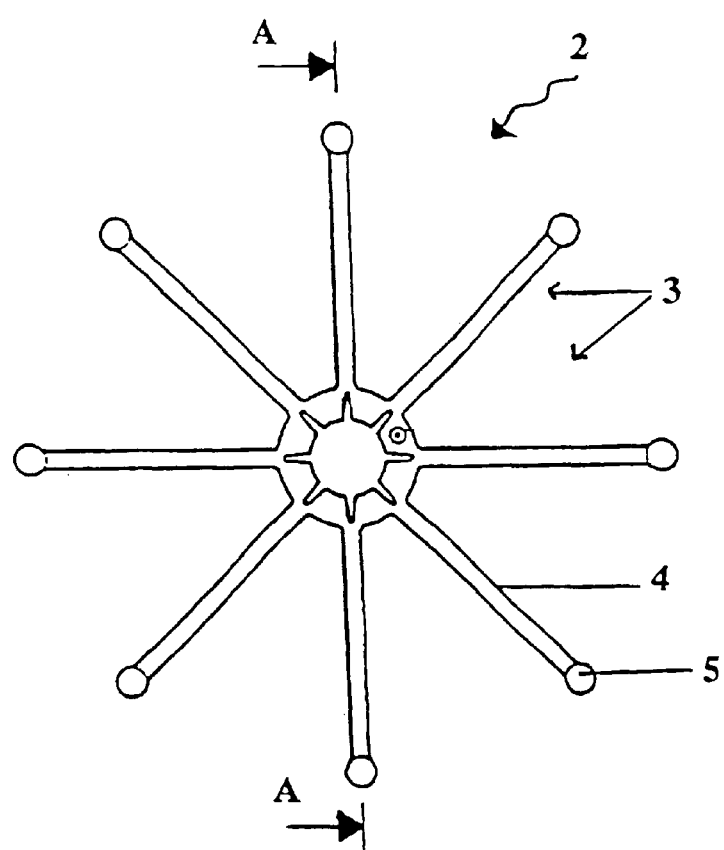
FIG. 3 is a diagrammatic top plan view of a retention apparatus in accordance with another embodiment of the present invention.
Figure 4:
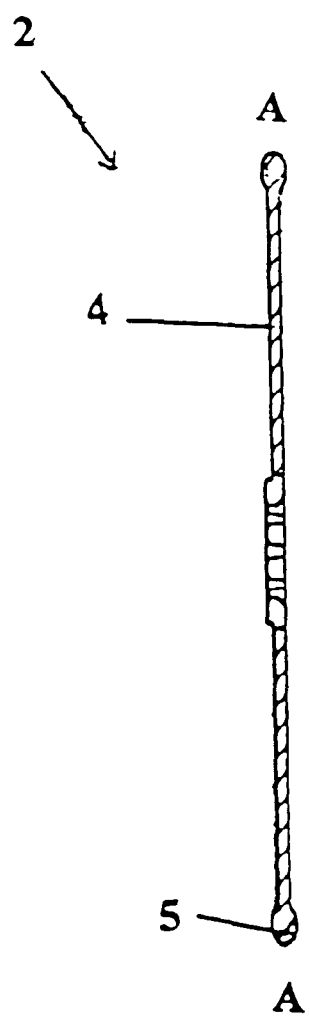
FIG. 4 is a diagrammatic cross section of the retention apparatus in FIG. 3, in accordance with that embodiment of the present invention.

FIGS. 1 and 2 are diagrammatic perspective views of the retention apparatus 2 for a device 1 capable of insertion into a body cavity of an animal, according to one embodiment of the present invention.

The multiple arms 3 of the retention apparatus 2 are substantially straight, thin and substantially circular to reduce the interference with the normal flow of body secretions, such as mucus in the vagina.

The shaft 4 of each arm 3 is substantially elongate to enable the retention apparatus 2 to engage with the walls of a body cavity of an animal. The tip 5 of each arm 3 has a substantially greater cross-sectional dimension than the shaft 4 of the arm 3. In preferred embodiments, the tip 5 is substantially bulbous which obviates problems of irritation of the internal walls of the animal's body cavity.

The arms 3 of the retention apparatus 2 are substantially flexible, which enables the arms 3 to be aligned for insertion into the body cavity of an animal, and also enables the arms 3 to withstand the forces of the internal peristaltic waves within the body cavity of the animal. The substantial flexibility of the arms 3 enables the arms 3 to bend in response to the peristaltic waves without breaking, and enables the arms 3 to return to their fully extended retaining position once the peristaltic waves have passed.

The arms 3 of the retention apparatus 2 are moulded as an integral part of the body of a device 1 to which the retention apparatus 2 is attached. In one preferred embodiment the arms 3 of the retention apparatus 2 are resiliently hinged 6 at the junction 7 between the shaft 4 of the arm 3 and the body of the device 1 (as in FIGS. 7 to 10 inclusive). Or in another preferred embodiment, the arms 3 are completely moulded to the body of the device 1 (as in FIGS. 5, 6, 11 and 12).

Figure 5:
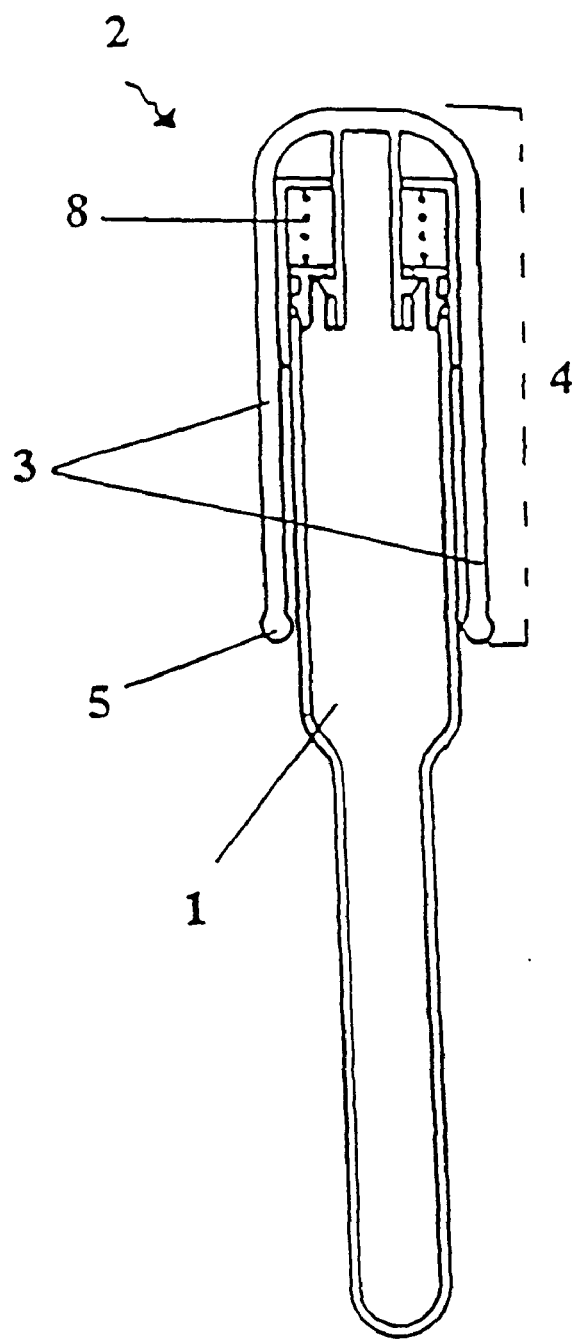
FIG. 5 is a diagrammatic cross-sectional view of a retention apparatus in accordance with one embodiment of the present invention.
Figure 6:
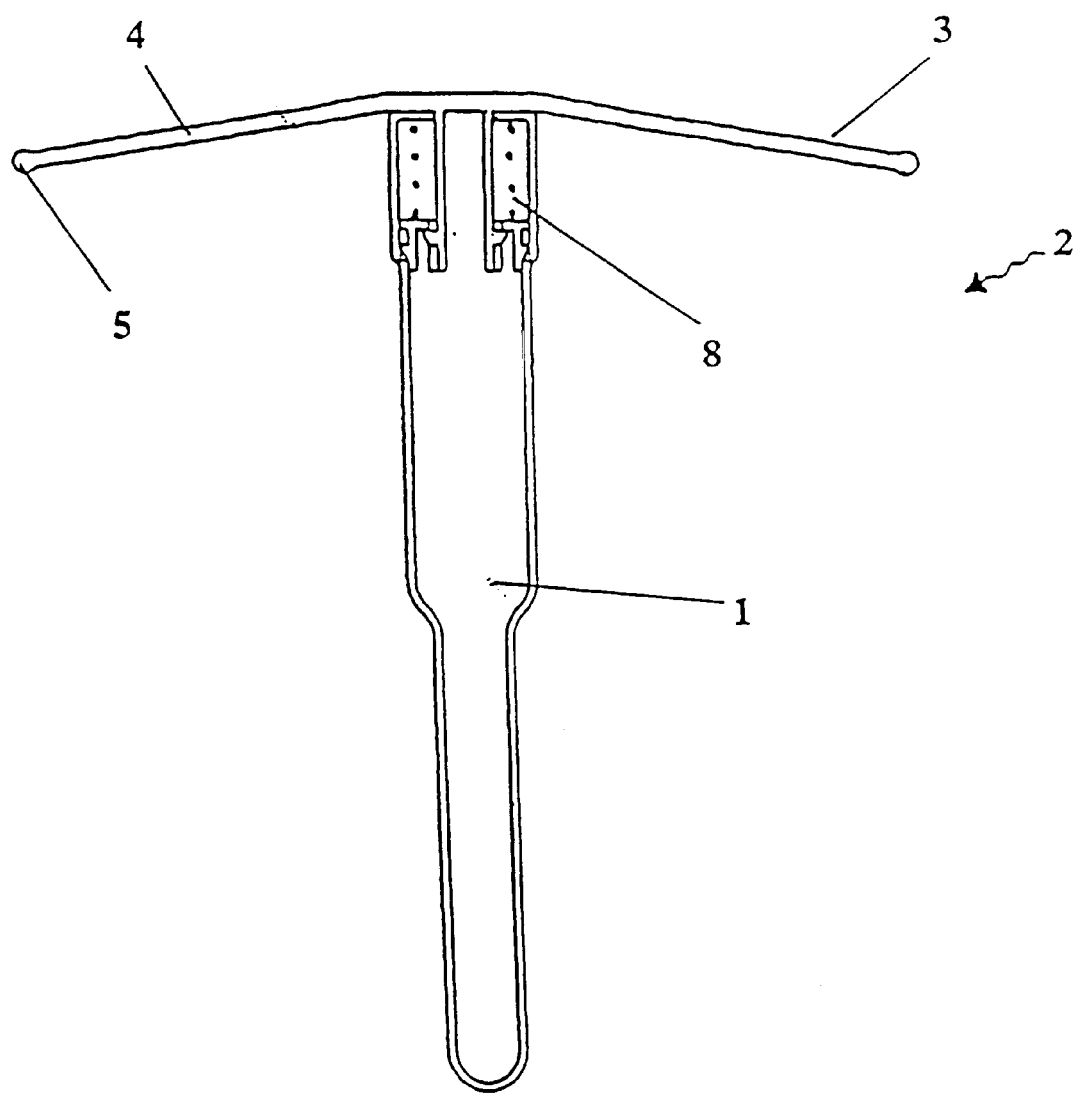
FIG. 6 is a diagrammatic cross-sectional view of a retention apparatus in accordance with another embodiment of the present invention.
Figure 7:
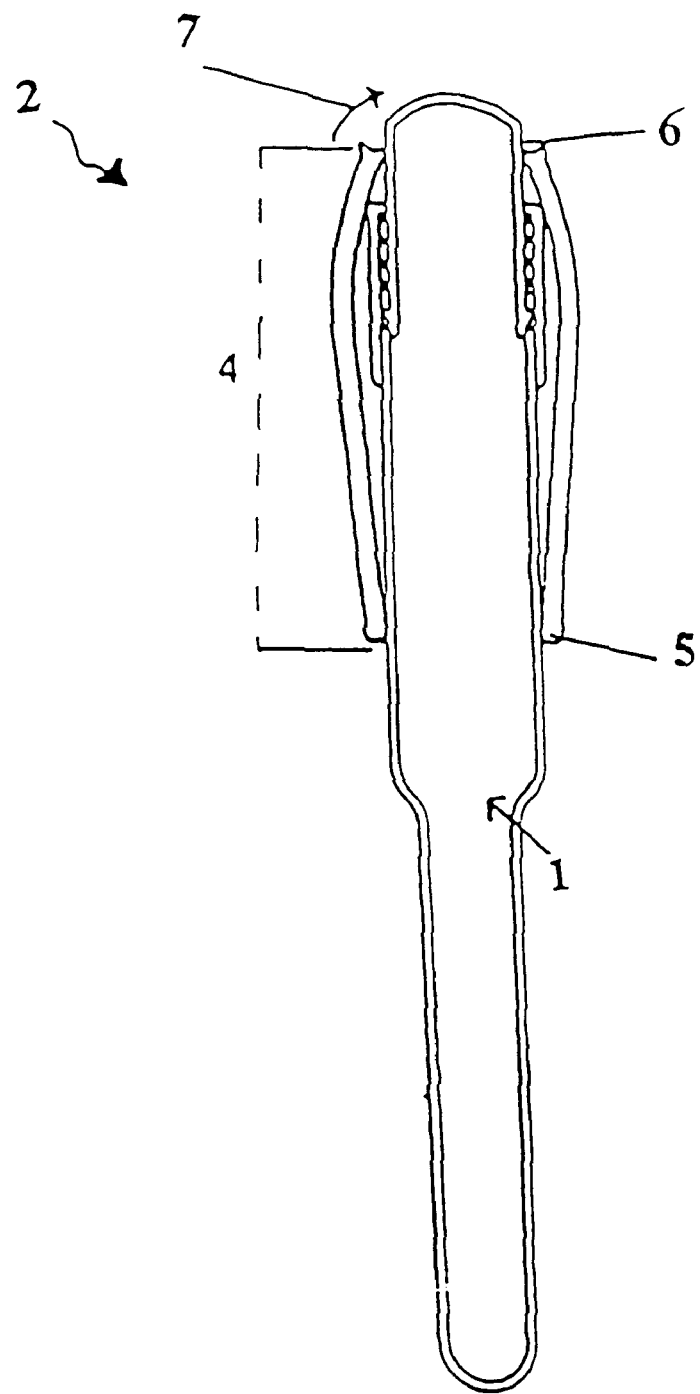
FIG. 7 is a diagrammatic cross-sectional view of a retention apparatus in accordance with another embodiment of the present invention.
Figure 8:
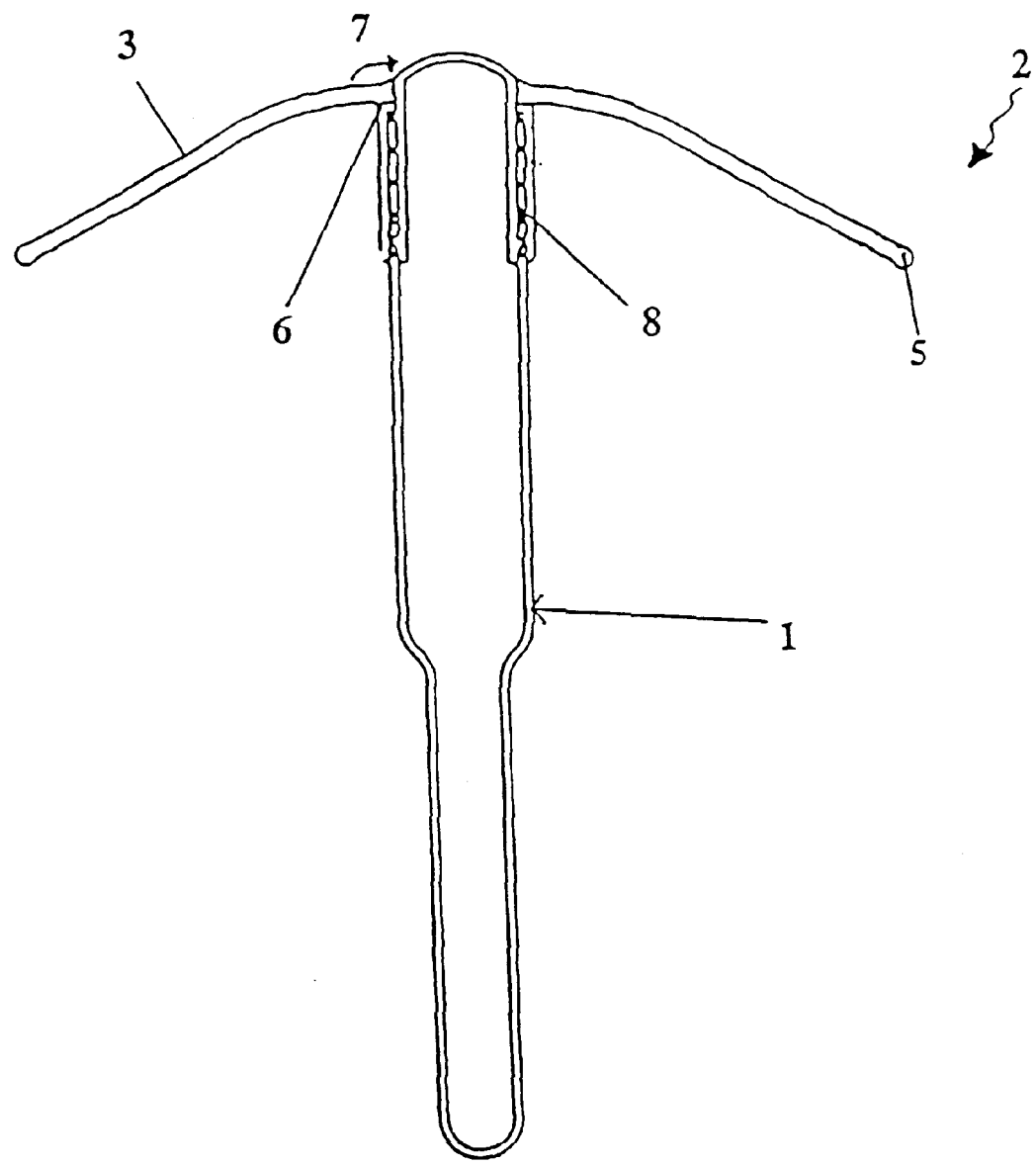
FIG. 8 is a diagrammatic cross-sectional view of a retention apparatus in accordance with another embodiment of the present invention.
Figure 9:
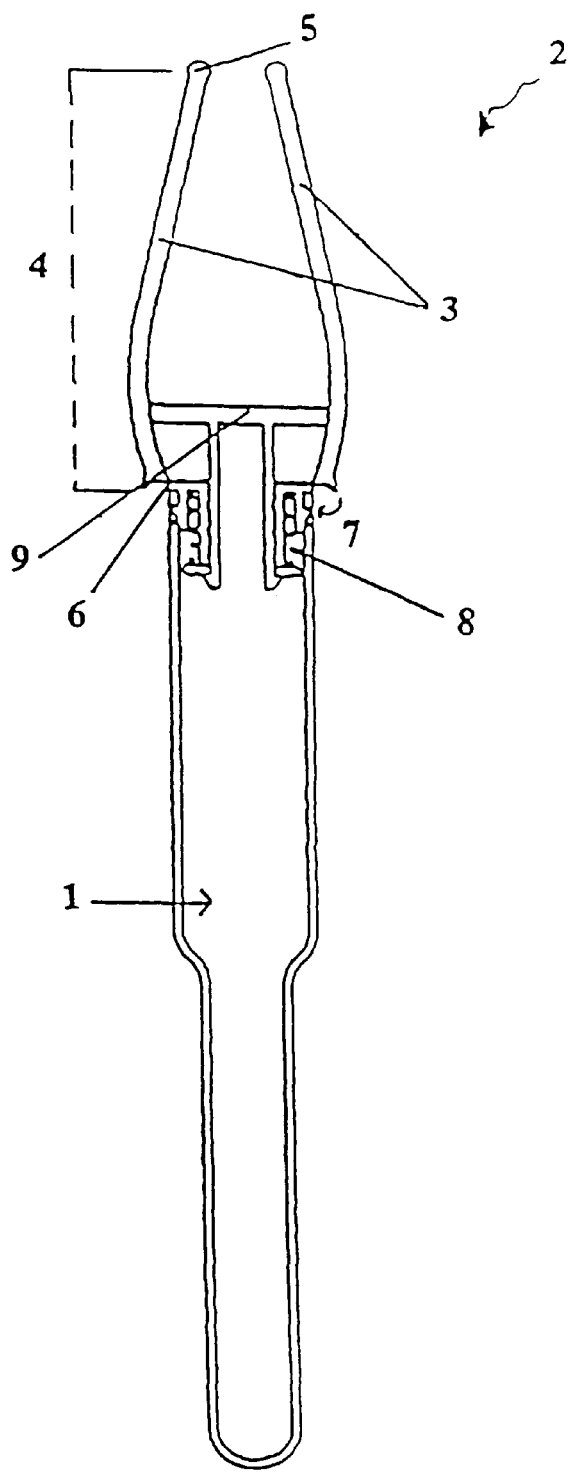
FIG. 9 is a diagrammatic cross-sectional view of a retention apparatus in accordance with another embodiment of the present invention.
Figure 10:
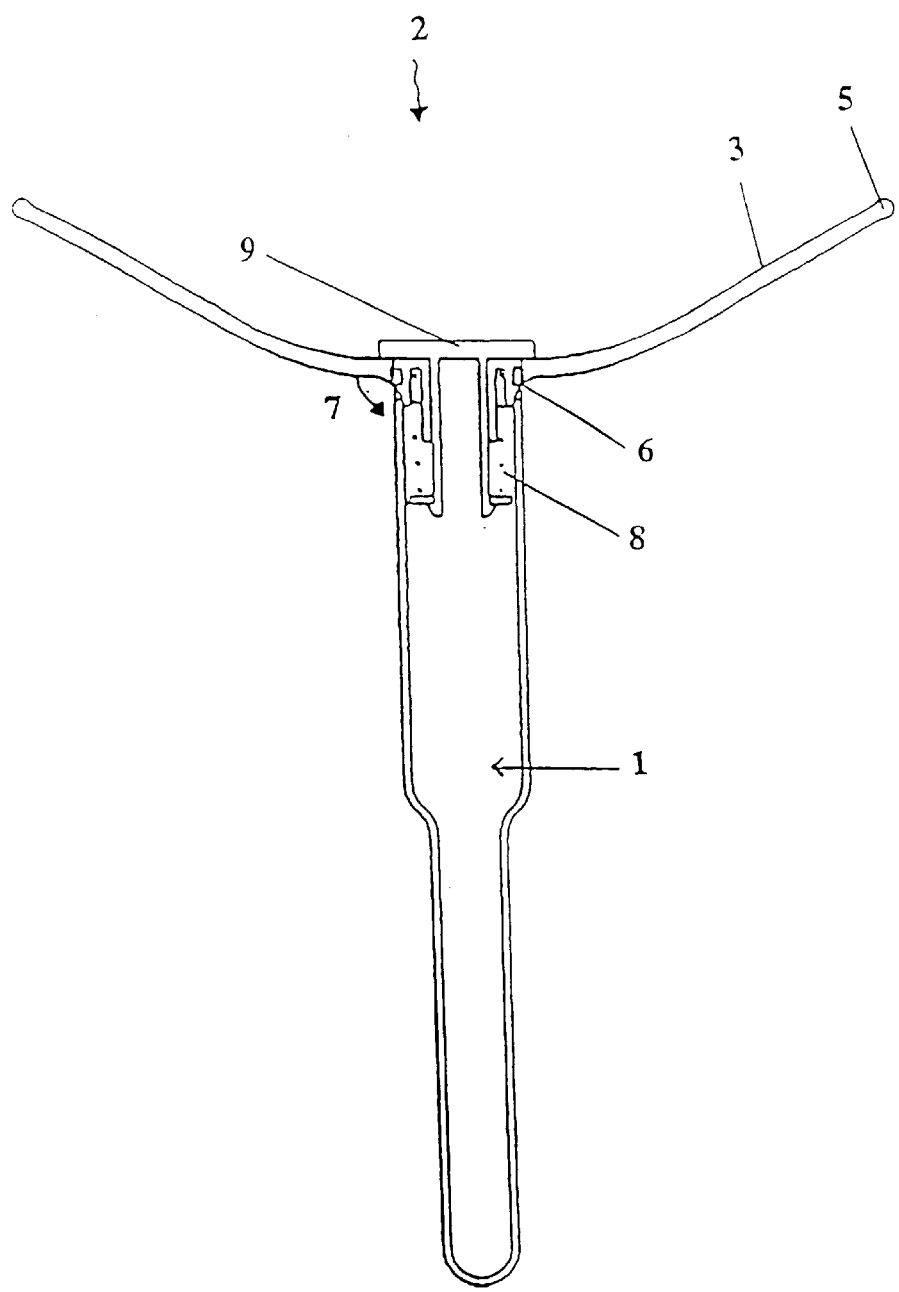
FIG. 10 is a diagrammatic cross-sectional view of a retention apparatus in accordance with another embodiment of the present invention.
Figure 11:
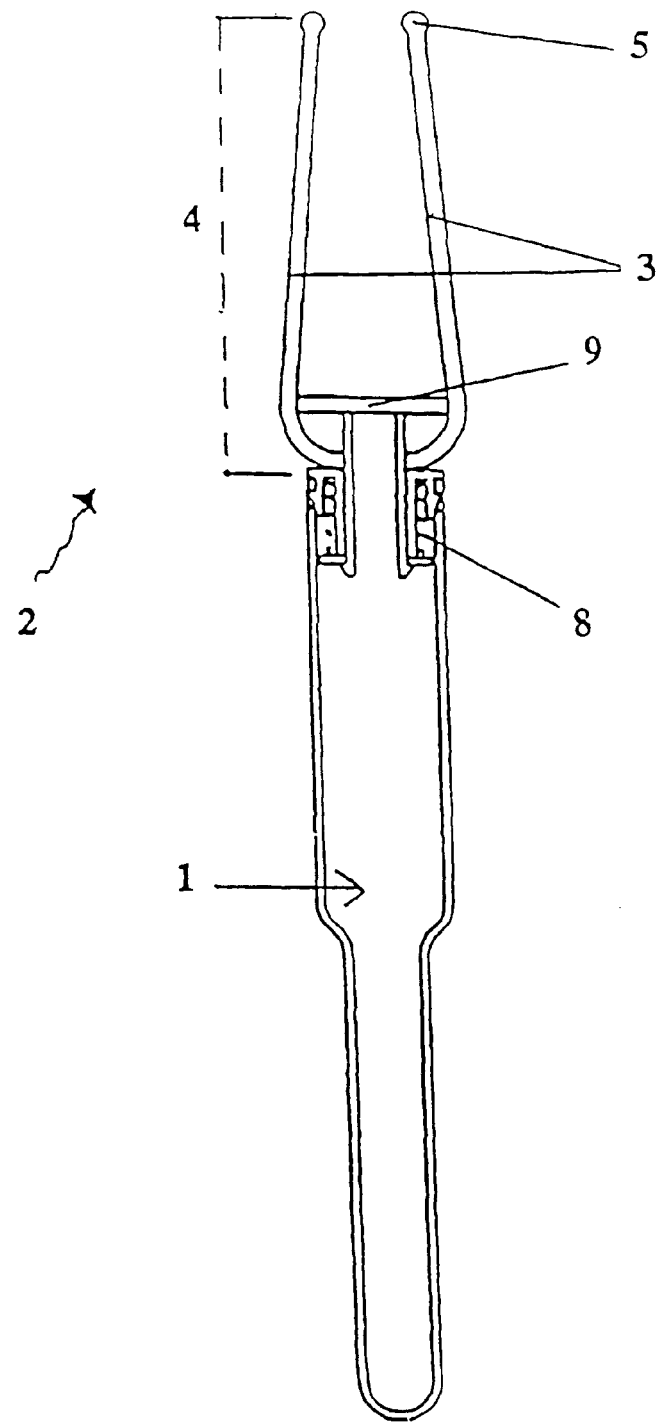
FIG. 11 is a diagrammatic cross-sectional view of a retention apparatus in accordance with another embodiment of the present invention.
Figure 12:
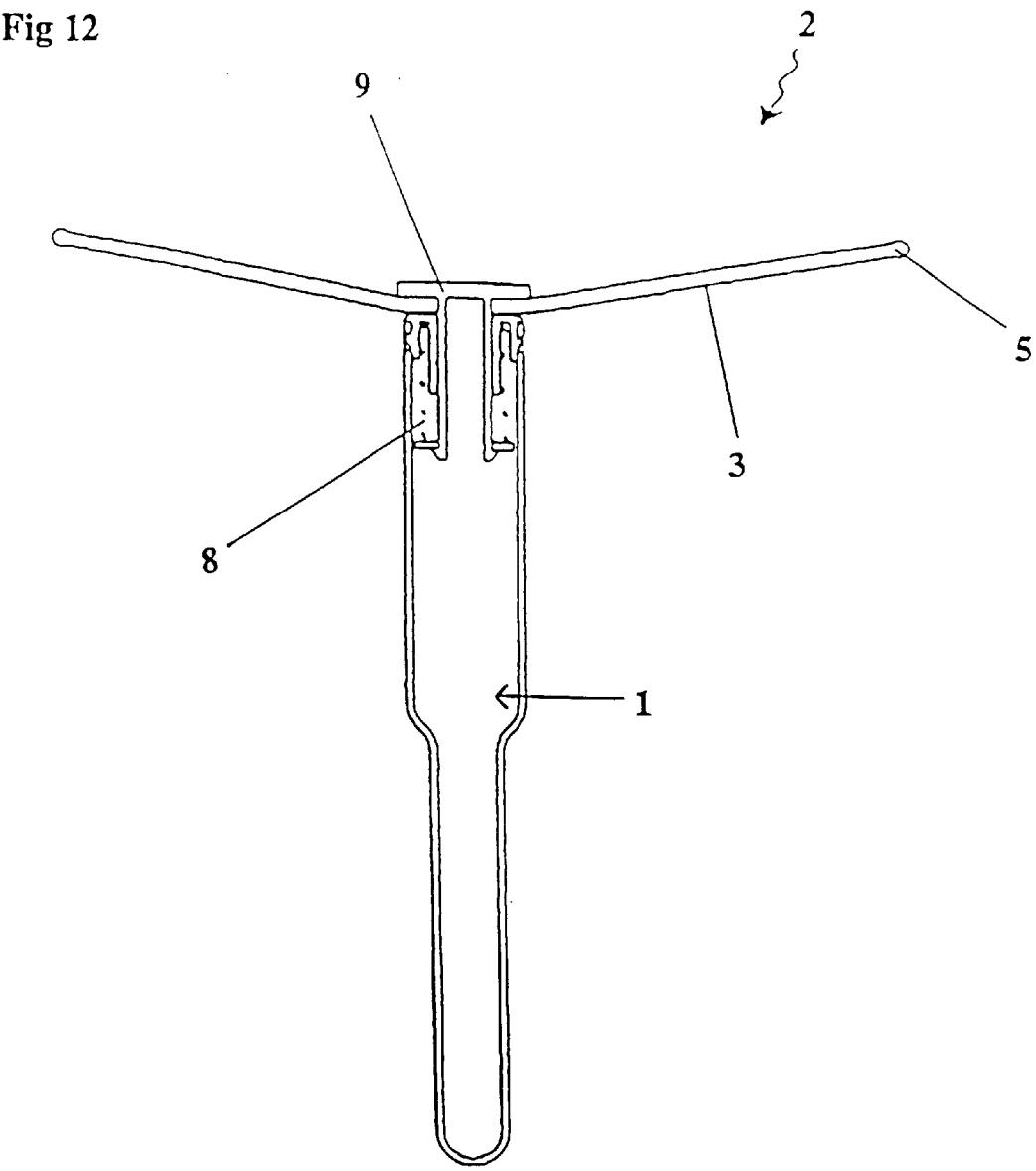
FIG. 12 is a diagrammatic cross-sectional view of a retention apparatus in accordance with another embodiment of the present invention.

The arms 3 of the retention apparatus 2 are operable between an aligned inserting position (as in FIGS. 5, 7, 9 and 11) and an extended retaining position (as in FIGS. 6, 8, 10 and 12). In the inserting position, the arms 3 are capable of being aligned substantially parallel to the body of the device 1 as shown in FIGS. 5 and 7. Alternatively, in other preferred embodiments the arms 3 of the retention apparatus 2 may be aligned with each other and the longitudinal axis of the device 1, as in FIGS. 9 and 11.

The arms 3 of the retention apparatus 2 are capable of being locked into the extended retaining position by the action of a spring-loaded collar 8. When the retention apparatus 2 is in its inserting position, the spring-loaded collar is cocked, as shown in FIGS. 5, 7, 9 and 11. During the process of insertion, when pressure is no longer applied to the arms 3 by an operator, an applicator, or the walls of the opening of the passage or body cavity into which the device is inserted, the arms 3 of the retention apparatus 2 are capable of moving towards the extended retaining position. This movement of the arms 3 activates the spring-loaded collar 8 to move in a direction substantially in-line with the longitudinal axis of the body of the device 1, and towards the arms 3. The spring-loaded collar 8 may operate in conjunction with the resiliently hinged arms 3 as in FIG. 8, or in conjunction with the substantially flexible arms 3, as in FIG. 6; by the action of the spring-loaded collar 8 in conjunction with a plunger 9 and resiliently hinged arms 3 as in FIG. 10, or by the action of a spring-loaded collar 8 in conjunction with plunger 9 and the substantial flexibility of the arms 3, as in FIG. 12.

The spring-loaded collar 8 operates to lock the arms 3 of the retention apparatus 2 in a plane substantially perpendicular to the body of the device 1. When locked in the extended retaining position the arms 3 of the retention apparatus 2 are located in a substantially radial arrangement around the body of the device 1 as in FIGS. 1 and 2.

Removal of the retention apparatus 2 may be effected by withdrawal of the device 1. During withdrawal of the substantially flexible arms 3 of the retention apparatus 2 may be realigned into a position substantially parallel to, or in line with the longitudinal axis of the body of the device 1. This alignment may be achieved through pressure exerted on the arms 3 by the walls of the animal's passage or body cavity through which the device is removed.

Figure 13:
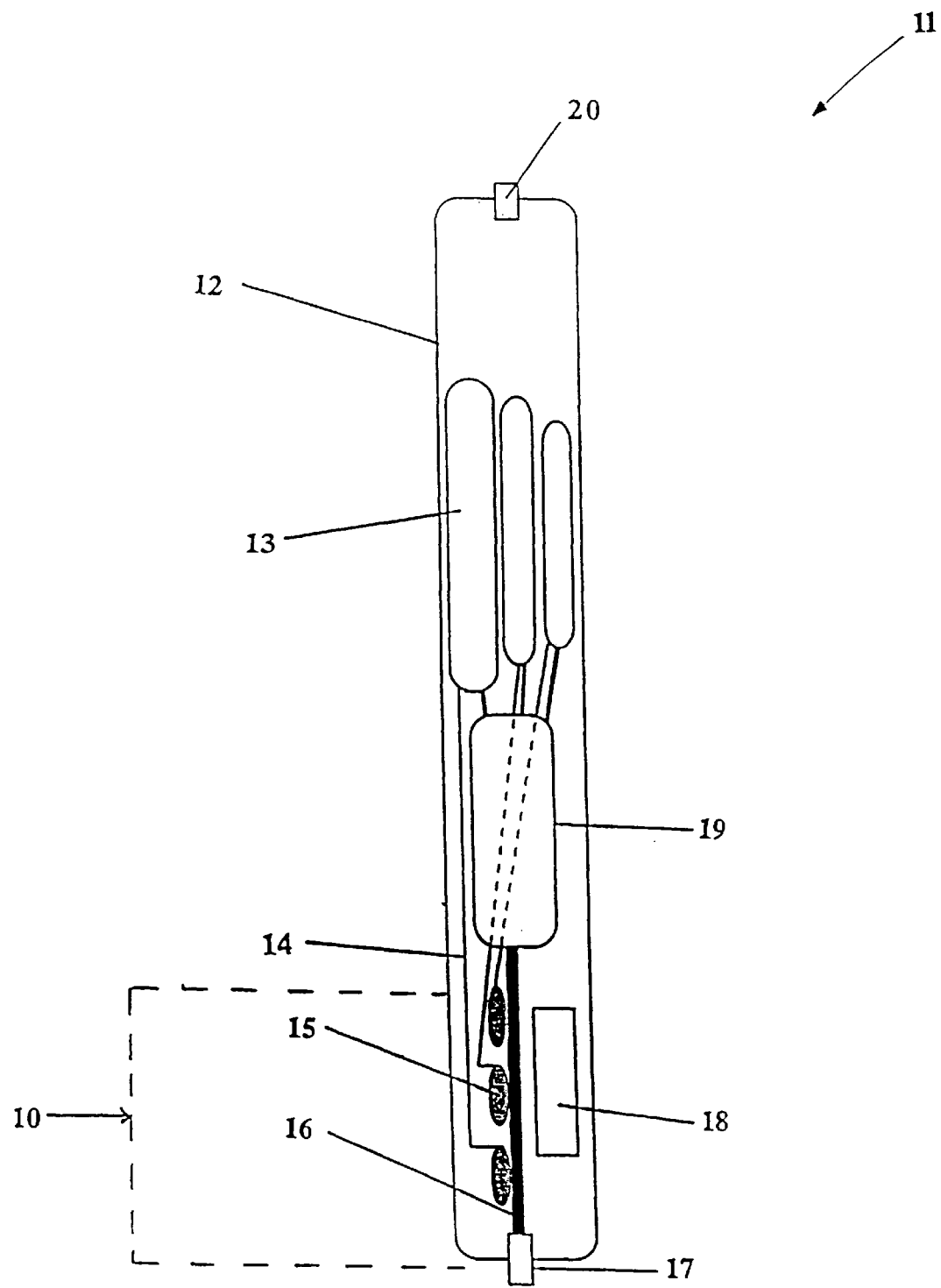
FIG. 13 is a diagrammatic view of a peristaltic device fitted in accordance with one embodiment of the present invention.

With respect to FIG. 13 there is illustrated a peristaltic device generally indicated by arrow 10 fitted into a delivery apparatus generally indicated by arrow 11.

The delivery apparatus 11 comprises a housing 12 containing reservoirs 13 containing the substances to be delivered by the delivery apparatus 11. The reservoirs 13 have connection lines 14 to three pressure devices in the form of piezo pumps 15.

A flexible conduit 16 leads to the outlet 17 of the delivery apparatus 11. The conduit 16 fits between three piezo pumps 15 and a pressure device controlling mechanism 18.

In this device 1 the controlling mechanism 18 is a microprocessor.

Also inside the housing 12 is an energy source 19 in the form of a battery and an inlet 20 that allows air into the housing 12 preventing the creation of a vacuum.

Figure 14:
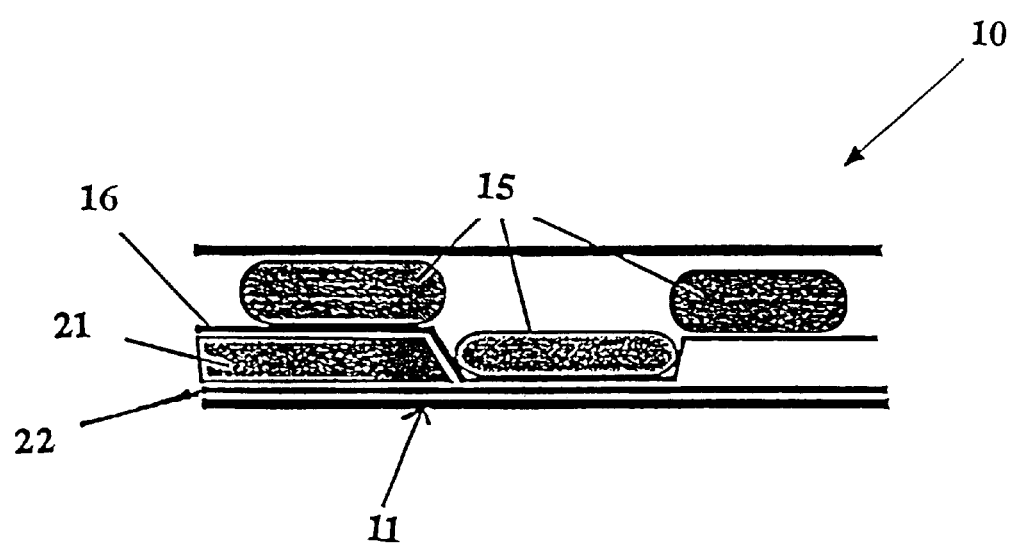
FIG. 14 is a view of the pressure device action on the flexible conduit.

FIG. 14 illustrates the action of the piezo pumps 15 on the flexible conduit 16.

If pressure from each pump 15 is sequentially applied to the flexible conduit 16, the substance 21 is forced along flexible conduit 16. The pumps 15 have restraints 22.

Operation of the present invention may occur as follows. The connection lines 14 may, cause substance holding bodies 13 to release substance into the flexible conduit 16. The pressure devices 15 apply pressure to the flexible conduit 16 to move the substance along the flexible conduit 16 to the substance outlet 17.

Figure 15:
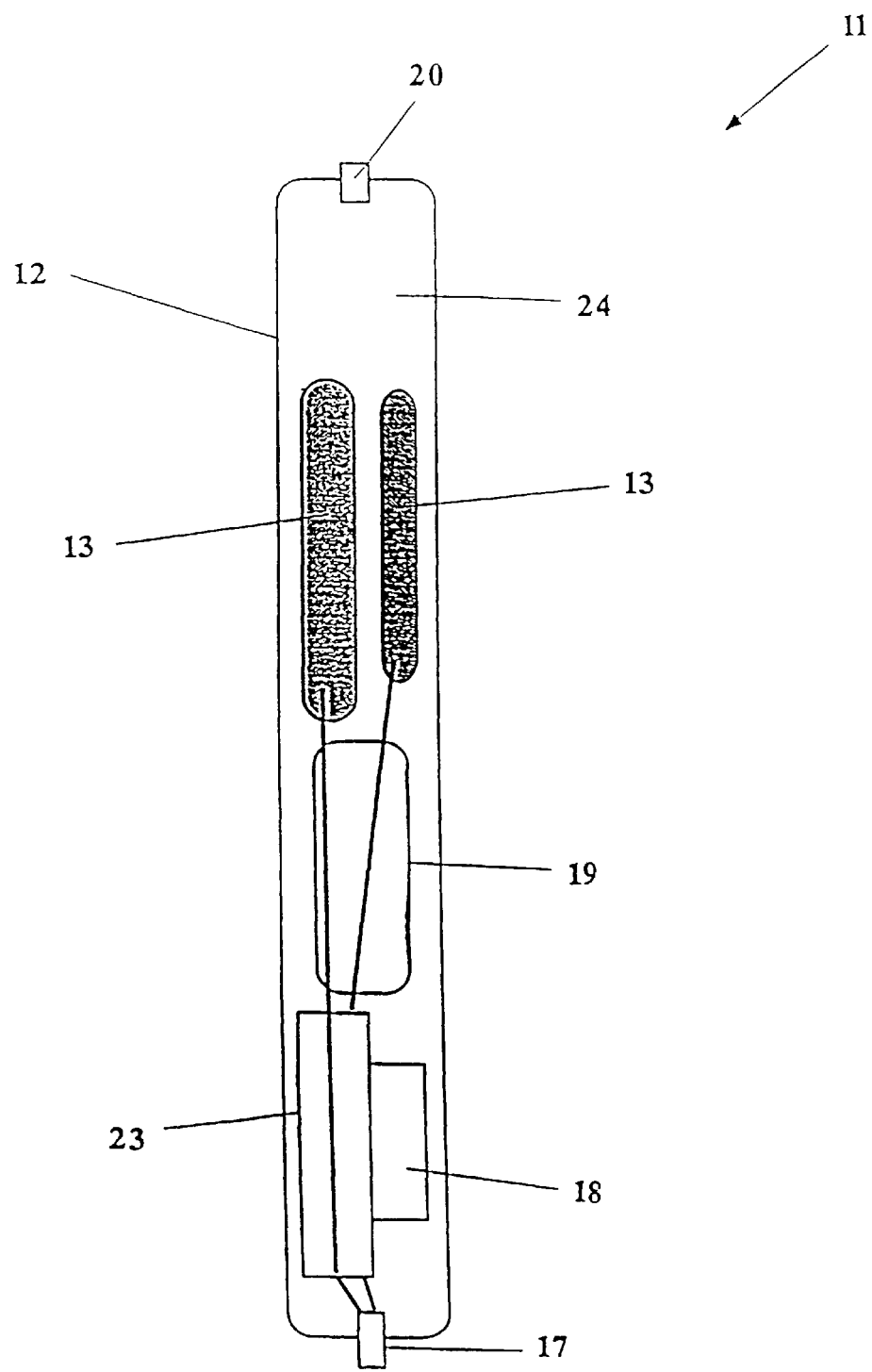
FIG. 15 is a diagrammatic view of a delivery apparatus which can be used in accordance with one embodiment of the present invention.
Figure 16:
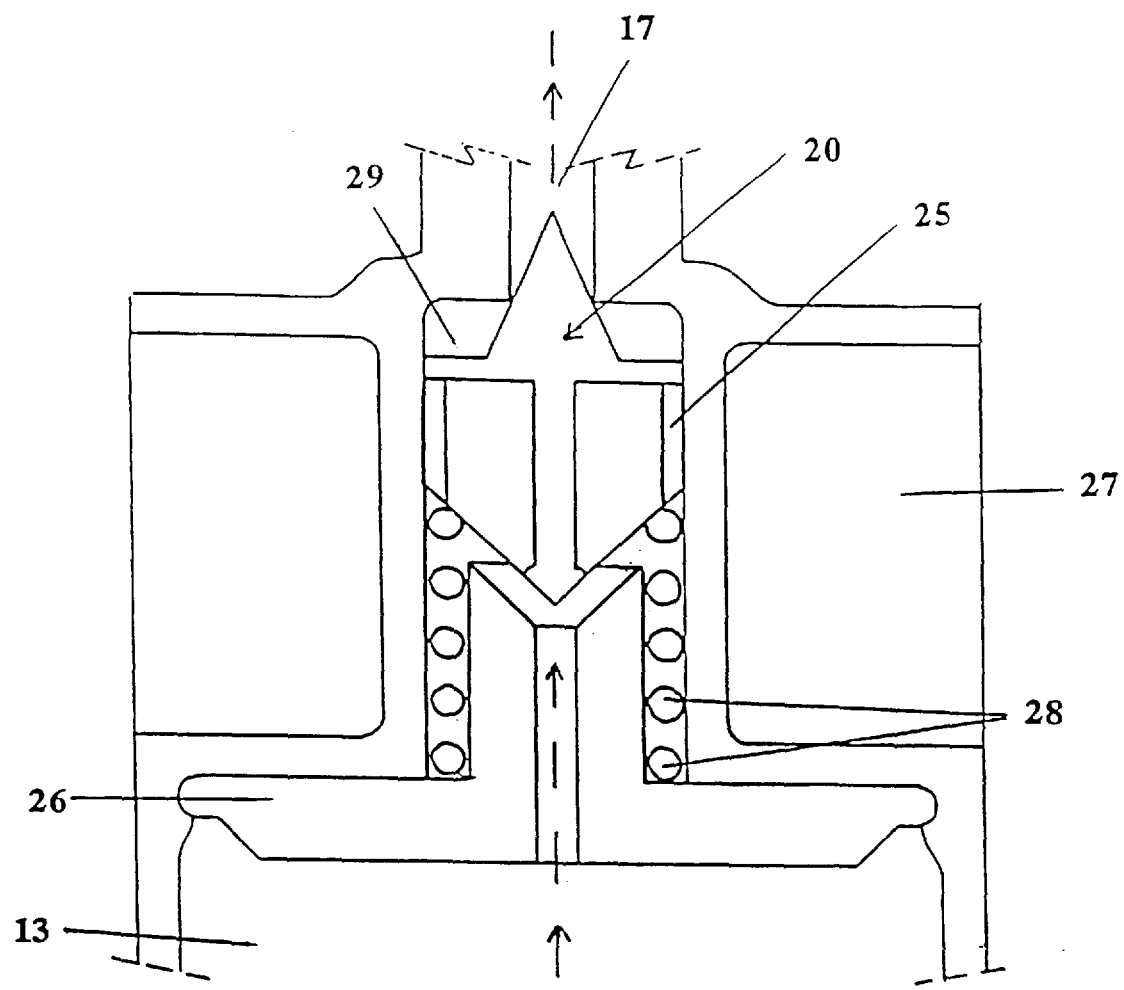
FIG. 16 is a diagrammatic ;view of a valve of a delivery apparatus used in accordance with a preferred embodiment of the present invention.
Figure 17:
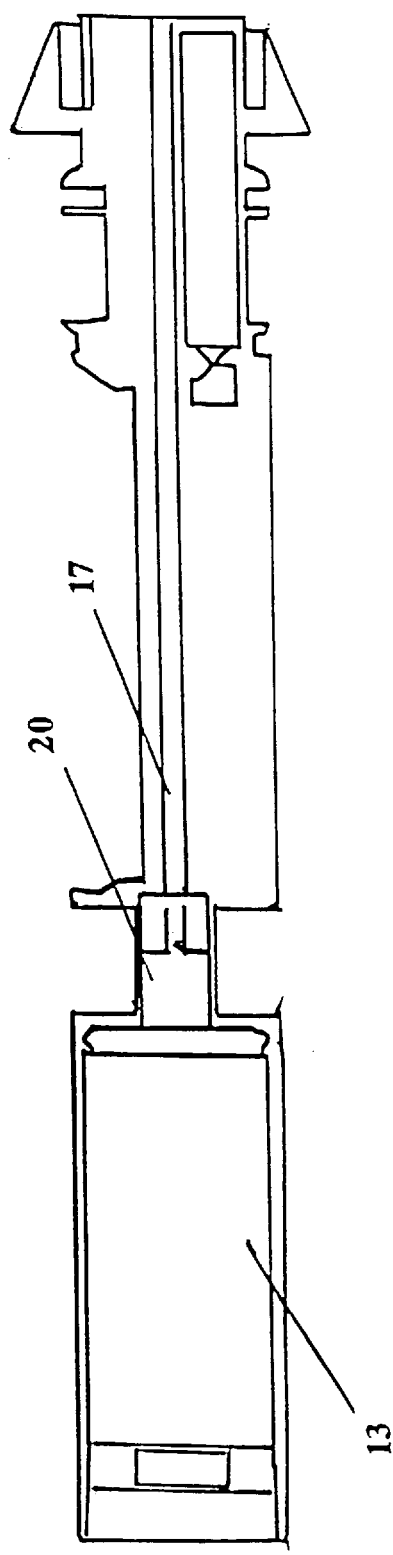
FIG. 17 is a diagrammatic cross-sectional view of a delivery apparatus used in accordance with a preferred embodiment of the present invention.
Figure 18:
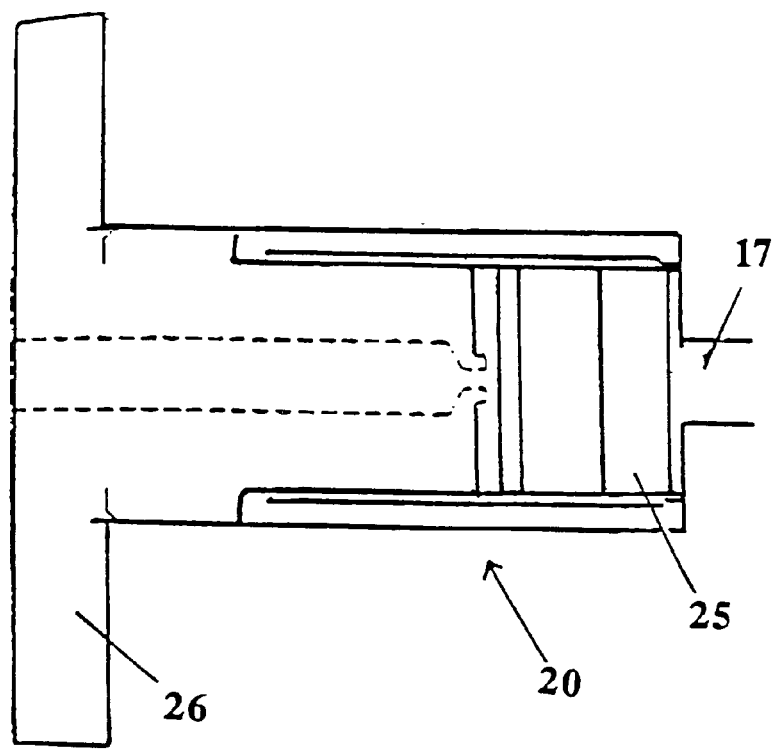
FIG. 18 is a diagrammatic view of an open valve of a delivery apparatus used in accordance with a preferred embodiment of the present invention.

FIG. 15 also illustrates the construction of a delivery apparatus 11. The deliver, apparatus 11 has an outer housing 12, an active delivery means in the form of a pump 23. a control means in the form of a microprocessor 18, an energy source in the form of a battery 19, and reservoirs 13 to hold the substances to be delivered.

In this embodiment, the reservoirs 13 are flexible walled and situated near one end of the delivery apparatus 11.

The inlet 20 comprises a one way valve 13 situated at the end of the housing 12. The inlet 20 leads into an air space 24 adjacent the reservoirs 13.

The reservoirs 13 are connected by conduits to the pump 23, which in turn is connected to an outlet 17 at the opposite end of the housing 12 to the one way valve 20.

In operation, the pump 13 and the microprocessor 18 are powered by the battery 19. The microprocessor 18 turns on the pump 13 and selects which of the substances in the reservoirs 13 are to be pumped through the conduits to the outlet 17 at a predetermined time. The pumping action causes air to enter the one way valve 20 and to air space 24. This allows the flexible wall containers to collapse under the air pressure as the substance is being pumped therefrom.

FIGS. 16, 17, 18 and 19 illustrates a metering valve 20 of a preferred embodiment of the present invention which operates on a reversed magnetic polarity principle.

The metering valve 20 consists of a moving armature 25 and a stationary armature 26. The armature 25 and 26 are preferably made out of soft iron or other magnetised material.

In this preferred embodiment, the reservoir 13 contains an active substance to be dispensed. The active substance is dissolved or suspended in a fluid, such that the resultant solution is of a low to modest viscosity, such as is found with weak aqueous solutions, alcohol, or light oil.

The reservoir 13 is pressurised. The pressure may be applied by a number of means, such as a spring and plunger system.

This embodiment relies on activation of a coil member 27. The coil member 27 is preferably operated at a low frequency and at a very low duty cycle. Typically however, the on off times of the coil member 27 will be greater than one second.

When the coil member 27 is activated, a solenoid action occurs. This in turn causes the moving armature 25 to be attracted to the stationary armature 26.

When the coil member 27 is turned off, the magnetising circuit decays. When the magnetising circuit decays, a volume of the active fluid solution which has passed from the reservoir 13 into a dosing chamber 29, and is equal in volume to the displaced diameter of the moving armature 25, is then pushed out of the outlet 17. The valve 20 includes a disk which acts as a non-return valve. Accordingly, this causes the displaced fluid to be pushed forward when the coil member 27 is de-energised.

While the coil member 27 is activated, the moving armature 25 is sealed against the stationary armature 26. This seal prevents the dosing chamber from being refilled from the reservoir 13. Accordingly, the dosing volume is relatively independent of the fluid reservoir pressure and the operating time of the valve 20.

A spring 28 is used to keep the moving armature 25 and the metering valve 20 seated on the outlet 17. The force of this spring 28 needs only be sufficient to ensure that the valve 20 seals reliably.

In some embodiments, metal laminations around the coil member 17 and within the outlet 17, may be used to improve the efficiency of the metering system.

Preferably, the stationary armature 26 is in contact with the fluid held in the reservoir 13. Accordingly, a suitable protective coating may be used to protect the stationary armature 26, and also the moving armature 25 from the effects of the fluid being dispensed.

In other embodiments of the present invention the moving armature 25 may be differently configured, to include a flat plate with laser drilled, or chemically milled cavities which form the dosing chamber(s).

Figure 19:
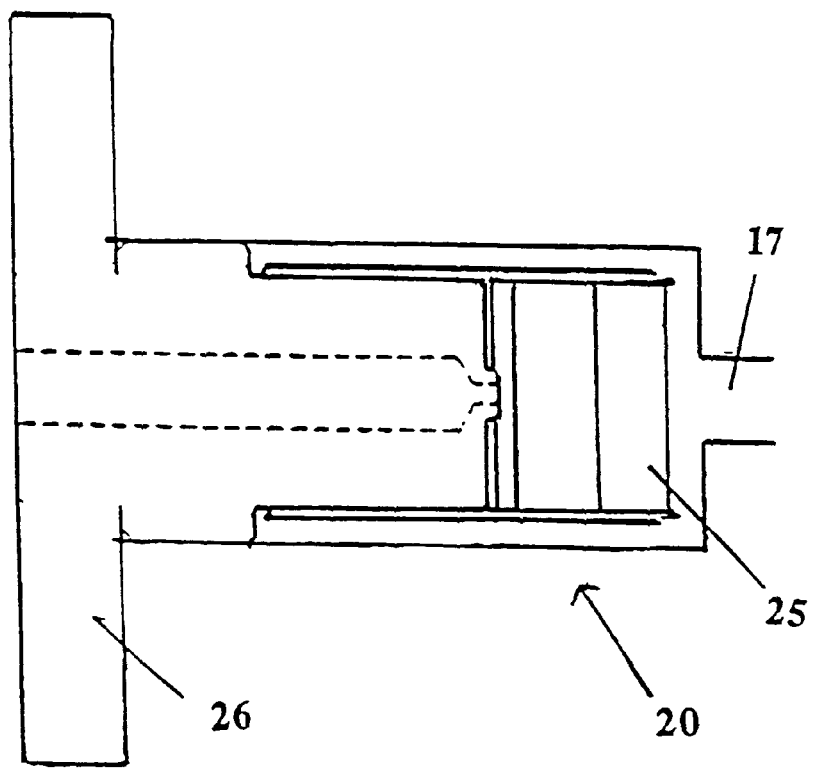
FIG. 19 is a diagrammatic view of a closed valve of a delivery apparatus used in accordance with a preferred embodiment of the present invention.
Figure 20:
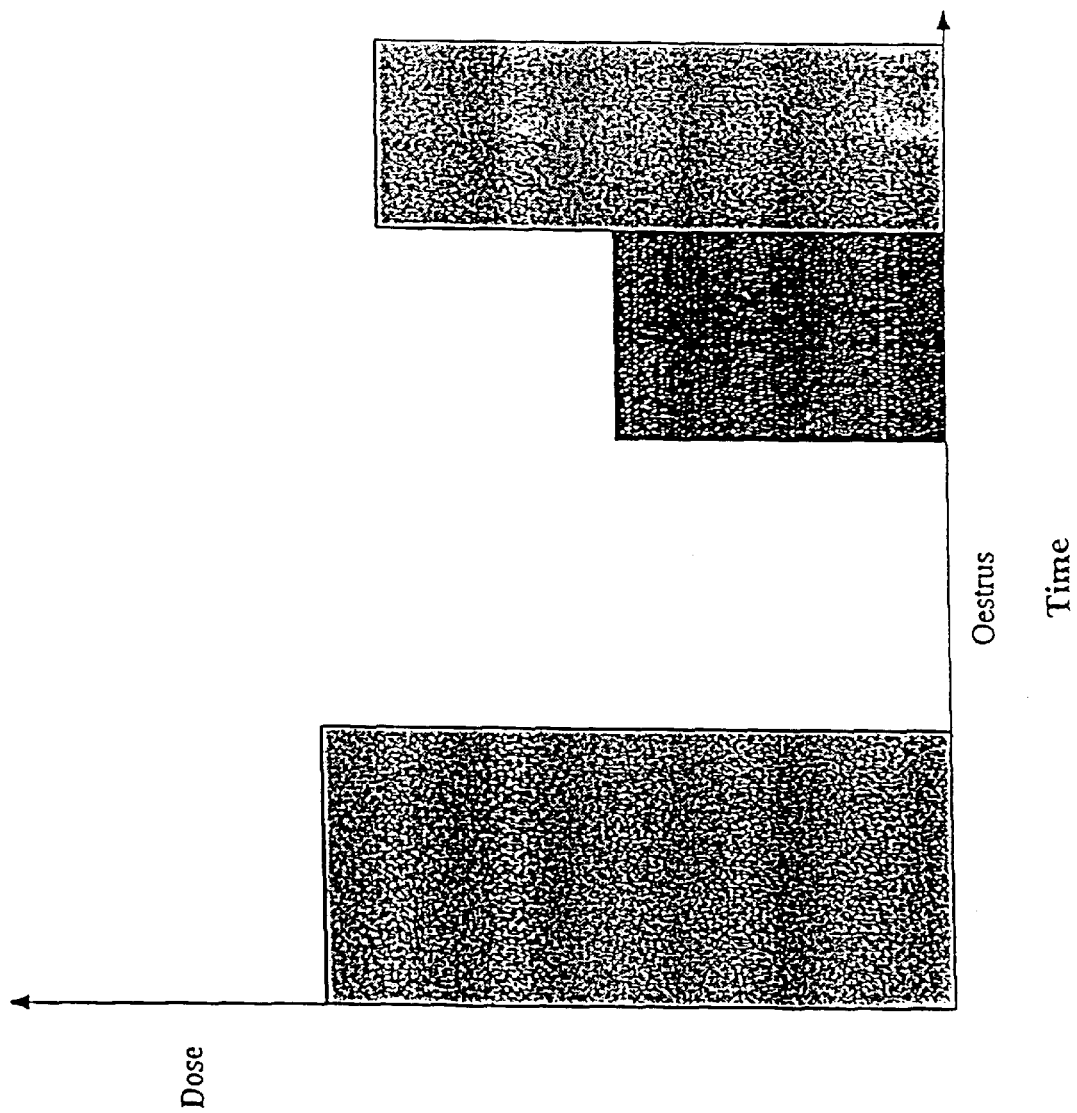
FIG. 20 is a graphical representation of a possible cycle which can be initiated with the present invention.

FIG. 19 illustrates a possible dosing scenario showing different doses of different hormones (indicated by different fill colours) being dispensed over predetermined times with the date of oestrus being positively defined.

Aspects of the present invention have been described by way of example only and it should be appreciated that modifications and additions may be made thereto without departing from the scope thereof, as defined in the appended claims.

The claims defining the invention are:

1. Substance delivery device for actively delivering at least one substance in either or both solid and fluid form into a body cavity of an animal into which the substance delivery device is inserted, said substance delivery device comprising:

a body having an outlet to the animal body cavity;

at least one reservoir within said body containing a substance;

means for applying pressure to said substance in said at least one reservoir for producing an expulsive force for delivering a predetermined dose of the substance under pressure from said at least one reservoir through said body outlet and into the animal body cavity;

means for actively controlling said means for applying pressure to effect delivery of the predetermined dose at a predetermined time; and retention apparatus attached to said body for engaging the walls of the animal body cavity for retaining said body in the animal body cavity during delivery of the substance.

2. Substance delivery device as in claim 1 wherein said at least one reservoir is of flexible material and said body has an opening to admit air to apply pressure to a said at least one reservoir to collapse it to aid in forcing the substance therethrough.

3. Substance delivery device as in claim 1 wherein said means for applying pressure to said substance in said at least one reservoir and effecting an expulsive force for delivering a predetermined dose of the substance under pressure from said at least one reservoir through said body outlet and into the animal body cavity comprises a peristaltic pump.

4. Substance delivery device as in claim 1 wherein said means for producing an expulsive force for delivering a predetermined dose of the substance under pressure from said at least one reservoir through said body outlet and into the animal body cavity comprises delivery means which operates to produce pressure on the substance, said delivery means comprising:

a conduit connected between said at least one reservoir and said body outlet; and a plurality of actuating members to sequentially apply force to a respective portion of said conduit.

5. Substance delivery device as in claim 4 wherein there are a plurality of reservoirs each having an outlet to said conduit which is in common with all of said reservoirs and said actuating members act on said common conduit.

6. Substance delivery device as in claim 4 wherein said actuating members comprise piezoelectric elements.

7. Substance delivery device as in claim 5 wherein each of said plurality of reservoirs is of flexible material and said body has an opening to admit air to apply pressure to each said reservoir to collapse it to aid in forcing the substance therethrough.

8. Substance delivery device as in claim 1 wherein said means for applying pressure to said substance in a said at least one reservoir and effecting an expulsive force for delivering a predetermined dose of the substance from said reservoir through said body outlet and into the animal body cavity is a delivery means which in operation effects pressure on the substance and includes means to actively control the delivery means to effect delivery of the predetermined dose at a predetermined time and which delivery means further comprises:

a conduit between said reservoir and said body outlet; and a pump in fluid communication with said conduit for withdrawing the substance from a said at least one reservoir.

9. Substance delivery device as in claim 8 wherein a said at least one reservoir is of flexible material and said body has an opening to admit air to apply pressure to a said at least one reservoir to collapse it to aid in forcing the substance therethrough.

10. Substance delivery device as in claim 1 wherein said means for applying pressure to said substance in a said at least one reservoir and effecting an expulsive force for delivering a predetermined dose of the substance from said at least one reservoir through said body outlet and into the animal body cavity is a delivery means which in operation effects pressure on the substance and said delivery means comprises:

means for pressuring said reservoir; and controllable valve means between an outlet of said reservoir and said body outlet.

11. Substance delivery device as in claim 10 wherein said controllable valve means comprises a magnetically responsive valve.

12. Substance delivery device as in claim 11 wherein said magnetically responsive valve comprises:

a valve housing having a first end with an opening to be in communication with the pressurized substance in a said at least one reservoir and a second end with an opening in communication with said body opening through which the substance is to be delivered into the animal body cavity.

13. Substance delivery device as in claim 12 further comprising a coil of wire around said valve housing to which current is supplied and removed to effect movement of said valve between said first and second ends of said valve housing.

14. Substance delivery device as in claim 13 wherein said valve normally closes said housing second end opening.

15. Substance delivery device as in claim 13 wherein as said valve moves to seal said opening at the first end of said valve housing, the substance is discharged from the said at least one reservoir through the valve first end into a central bore of the valve housing.

16. Substance delivery device as in claim 13 wherein as current is applied to said coil said valve housing first end opening is sealed by said valve and as the current is released said valve moves to seal said valve housing second end opening and during movement to seal said housing second end opening expels the substance out through the opening of said housing second end.

17. Substance delivery device as in claim 10 wherein said means for pressurizing comprises a spring and plunger system.

18. Substance delivery device as in claim 10 wherein said controllable valve means opens and closes in response to the pressure applied to the said at least one reservoir.

19. Substance delivery device as in claim 1 wherein there are a plurality of said reservoirs within said device body and said means for applying pressure to said substance in said plurality of reservoirs and effecting an expulsive force for delivering a predetermined dose of the substance under pressure from a said reservoir through said body outlet and into the animal body cavity selectively operates to expel the substance from any one of said reservoirs through said body outlet and into the animal body cavity.

20. Substance delivery device as in claim 1 wherein said retention apparatus comprises:

a plate to be securely located at least one end of said body;

retention means comprising a plurality of longitudinal arms for extending generally radially from either or both of said plate and said body, the ends of said arms distal from said plate or said body being adapted to contact with an internal surface that defines the animal body cavity;

said arms being flexible to be foldable from a condition for insertion into the animal body cavity to one after insertion of the cavity wherein said arms revert to a retaining condition to maintain continual contact with at least a portion of at least one of said arms lying against the surface of the body cavity for preventing passage of the device through the cavity and/or inadvertent removal.

* * * * *

UNITED STATES PATENT AND TRADEMARK OFFICE
CERTIFICATE OF CORRECTION

PATENT NO. : 6,962,579 B2  
DATED : November 8, 2005  
INVENTOR(S) : Hugh P. Jellie It is certified that error appears in the above-identified patent and that said Letters Patent is hereby corrected as shown below:

<u>Title page,</u>
Insert Item -- [30]   Foreign Application Priority Data
              New Zealand        270794      March 23, 1995 --.

Signed and Sealed this

Fourth Day of April, 2006

JON W. DUDAS
*Director of the United States Patent and Trademark Office*